US011633233B2

(12) United States Patent
Lavallee et al.

(10) Patent No.: US 11,633,233 B2
(45) Date of Patent: Apr. 25, 2023

(54) SURGICAL SYSTEM FOR CUTTING AN ANATOMICAL STRUCTURE ACCORDING TO AT LEAST ONE TARGET CUTTING PLANE

(71) Applicant: Orthotaxy, La Tronche (FR)

(72) Inventors: Stéphane Lavallee, Saint Martin d'Uriage (FR); Daniel Girardeau-Montaut, Grenoble (FR); Hervé Collet, Chatenay (FR); Anthony Leandri, Crolles (FR); Nicolas Demanget, Saint-Egrève (FR)

(73) Assignee: Orthotaxy S.A.S., Gières (FR)

( * ) Notice: Subject to any disclaimer, the term of this patent is extended or adjusted under 35 U.S.C. 154(b) by 861 days.

(21) Appl. No.: 16/467,824

(22) PCT Filed: Dec. 8, 2017

(86) PCT No.: PCT/EP2017/082041
§ 371 (c)(1),
(2) Date: Jun. 7, 2019

(87) PCT Pub. No.: WO2018/104523
PCT Pub. Date: Jun. 14, 2018

(65) Prior Publication Data
US 2022/0047329 A1 Feb. 17, 2022

(30) Foreign Application Priority Data

Dec. 8, 2016 (EP) ..................................... 16306645
Dec. 8, 2016 (EP) ..................................... 16306646

(Continued)

(51) Int. Cl.
*A61B 18/20* (2006.01)
*A61B 17/14* (2006.01)
(Continued)

(52) U.S. Cl.
CPC .............. *A61B 18/20* (2013.01); *A61B 17/00* (2013.01); *A61B 17/142* (2016.11); *A61B 34/20* (2016.02);
(Continued)

(58) Field of Classification Search
CPC .................................................... A61B 17/142
See application file for complete search history.

(56) References Cited

U.S. PATENT DOCUMENTS 5,236,432 A 8/1993 Matsen et al.
5,748,767 A 5/1998 Raab et al.
(Continued)

FOREIGN PATENT DOCUMENTS

CN 1243690 A 2/2000
CN 101484086 A 7/2009
(Continued)

OTHER PUBLICATIONS

Roth et al., "A New Less Invasive Approach to Knee Surgery Using a Vision-Guided Manipulator", Virtual Reality, Montpellier, France, Dec. 2000, 8 pages.
(Continued)

*Primary Examiner* — Christian A Sevilla
(74) *Attorney, Agent, or Firm* — Condo Roccia Koptiw LLP

(57) ABSTRACT

The invention relates to a surgical system for cutting an anatomical structure (F, T) of a patient according to at least one target plane defined in a coordinate system of the anatomical structure, comprising: (i) a robotic device (100) comprising: —an end effector (2), —an actuation unit (4) having at least three motorized degrees of freedom, configured for adjusting a position and orientation of the end effector (2) relative to each target plane, —a passive planar mechanism (24) connecting the terminal part (40) of the (Continued)

actuation unit (4) to the end effector (2); (ii) a tracker (203) rigidly attached to the end effector (2), (iii) a tracking unit (200) configured to determine in real time the pose of the end effector (2) with respect to the coordinate system of the anatomical structure, a control unit (300) configured to determine the pose of the end effector with respect to the target plane and to control the actuation unit so as to bring the cutting plane into alignment with the target plane.

20 Claims, 13 Drawing Sheets

(30) Foreign Application Priority Data

Oct. 25, 2017 (WO) ................ PCT/EP2017/077370
Dec. 7, 2017 (WO) ................ PCT/EP2017/081803

(51) Int. Cl.
*A61B 34/20* (2016.01)
*A61B 34/30* (2016.01)
*B25J 15/04* (2006.01)
*A61B 17/00* (2006.01)

(52) U.S. Cl.
CPC ............ *A61B 34/30* (2016.02); *B25J 15/0408* (2013.01); *A61B 2034/2051* (2016.02); *A61B 2034/2055* (2016.02)

(56) References Cited

U.S. PATENT DOCUMENTS

| | | | |
|---|---|---|---|
| 5,871,018 A | 2/1999 | Delp et al. | |
| 6,033,415 A | 3/2000 | Mittelstadt et al. | |
| 6,205,411 B1 | 3/2001 | Digioia et al. | |
| 6,246,200 B1 | 6/2001 | Blumenkranz et al. | |
| 6,322,567 B1 | 11/2001 | Mittelstadt et al. | |
| 6,533,737 B1 | 3/2003 | Brosseau et al. | |
| 6,554,837 B1 | 4/2003 | Hau et al. | |
| 6,757,582 B2 | 6/2004 | Brisson et al. | |
| 6,788,018 B1 | 9/2004 | Blumenkranz et al. | |
| 7,035,716 B2 | 4/2006 | Harris et al. | |
| 7,206,626 B2 | 4/2007 | Quaid et al. | |
| 7,206,627 B2 | 4/2007 | Abovitz et al. | |
| 7,346,417 B2 | 3/2008 | Luth et al. | |
| 7,747,311 B2 | 6/2010 | Quaid et al. | |
| 7,831,292 B2 | 11/2010 | Quaid et al. | |
| 8,010,180 B2 | 8/2011 | Quaid et al. | |
| 8,095,200 B2 | 1/2012 | Quaid et al. | |
| 8,287,522 B2 | 10/2012 | Moses et al. | |
| 8,396,598 B2 | 3/2013 | Sutherland et al. | |
| 8,460,277 B2 | 6/2013 | Suare et al. | |
| 8,506,555 B2 | 8/2013 | Ruiz et al. | |
| 8,518,051 B2 | 8/2013 | Shoham et al. | |
| 8,838,205 B2 | 9/2014 | Shoham et al. | |
| 8,882,777 B2 | 11/2014 | Heavener et al. | |
| 9,043,023 B2 | 5/2015 | Noro | |
| 9,060,794 B2 | 6/2015 | Kang et al. | |
| 9,119,655 B2 | 9/2015 | Bowling et al. | |
| 9,149,281 B2 | 10/2015 | Bonutti et al. | |
| 9,220,510 B2 | 12/2015 | Cheal et al. | |
| 9,226,796 B2 | 1/2016 | Bowling et al. | |
| 9,271,804 B2 | 3/2016 | Wu et al. | |
| 9,275,192 B2 | 3/2016 | Kang et al. | |
| 9,289,264 B2 | 3/2016 | Iorgulescu et al. | |
| 9,364,291 B2 | 6/2016 | Bellettre et al. | |
| 9,492,237 B2 | 11/2016 | Kang et al. | |
| 9,665,686 B2 | 5/2017 | Van et al. | |
| 9,724,165 B2 | 8/2017 | Arata et al. | |
| 9,743,936 B2 | 8/2017 | Huet et al. | |
| 9,812,035 B2 | 11/2017 | Stuart et al. | |
| 9,814,468 B2 | 11/2017 | Kang et al. | |
| 9,827,115 B2 | 11/2017 | Walker et al. | |
| 9,901,356 B2 | 2/2018 | Shen et al. | |
| 9,937,014 B2 | 4/2018 | Bowling et al. | |
| 10,004,565 B2 | 6/2018 | Kang et al. | |
| 10,028,789 B2 | 7/2018 | Quaid et al. | |
| 10,064,689 B2 | 9/2018 | Swarup et al. | |
| 10,105,149 B2 | 10/2018 | Haider et al. | |
| 10,383,638 B2 | 8/2019 | Cheal et al. | |
| 10,653,488 B2 | 5/2020 | Kang et al. | |
| 11,154,369 B2 | 10/2021 | Roldan et al. | |
| 11,278,296 B2 | 3/2022 | Otto et al. | |
| 2005/0171553 A1 | 8/2005 | Schwarz | |
| 2005/0234465 A1* | 10/2005 | McCombs | A61B 17/155 606/88 |
| 2006/0015114 A1 | 1/2006 | Bernardoni et al. | |
| 2006/0142657 A1* | 6/2006 | Quaid | A61B 17/1703 600/424 |
| 2007/0137372 A1 | 6/2007 | Devengenzo et al. | |
| 2007/0156157 A1 | 7/2007 | Nahum et al. | |
| 2008/0010706 A1 | 1/2008 | Moses et al. | |
| 2008/0208081 A1* | 8/2008 | Murphy | A61B 90/36 600/595 |
| 2009/0228145 A1 | 9/2009 | Hodgson et al. | |
| 2009/0248044 A1* | 10/2009 | Amiot | G06F 30/17 606/130 |
| 2010/0016859 A1* | 1/2010 | Plassky | A61B 17/157 606/87 |
| 2011/0130761 A1 | 6/2011 | Plaskos et al. | |
| 2014/0236159 A1 | 8/2014 | Haider et al. | |
| 2016/0113728 A1 | 4/2016 | Piron et al. | |
| 2016/0135816 A1 | 5/2016 | Lavallee et al. | |
| 2016/0206375 A1 | 7/2016 | Abbasi et al. | |
| 2017/0079731 A1 | 3/2017 | Griffiths et al. | |
| 2018/0071114 A1* | 3/2018 | Walker | A61B 90/36 |
| 2020/0323540 A1 | 10/2020 | Kang et al. | |

FOREIGN PATENT DOCUMENTS

| | | |
|---|---|---|
| CN | 101919736 A | 12/2010 |
| CN | 102778848 A | 11/2012 |
| CN | 103300906 A | 9/2013 |
| CN | 103764061 A | 4/2014 |
| CN | 105050527 A | 11/2015 |
| CN | 105431102 A | 3/2016 |
| CN | 106132335 A | 11/2016 |
| CN | 106132345 A | 11/2016 |
| CN | 110076774 A | 8/2019 |
| DE | 102011004370 A1 | 8/2012 |
| EP | 456103 A2 | 11/1991 |
| EP | 2529910 A1 | 12/2012 |
| EP | 3007637 A1 | 4/2016 |
| JP | 2009-520573 A | 5/2009 |
| JP | 2016-523614 A | 8/2016 |
| WO | WO 2004-019785 A2 | 3/2004 |
| WO | 2007/045810 A2 | 4/2007 |
| WO | 2007/075864 A1 | 7/2007 |
| WO | 2012/131658 A1 | 10/2012 |
| WO | 2012/131660 A1 | 10/2012 |
| WO | 2014/198784 A1 | 12/2014 |
| WO | 2016/126914 A1 | 8/2016 |

OTHER PUBLICATIONS

Taylor, et al., "An Image-Directed Robotic System for Precise Orthopaedic Surgery", IEEE Transactions on Robotics and Automation, vol. 10, No. 3, Jun. 1994, 15 pages.

Kerschbaumer, et al., "A Mechatronic System for the Implantation of the Acetabular Component in Total Hip Alloarthroplasy", University of Siegen, Hoelderlinstr, 2001, 2 pages.

* cited by examiner

SURGICAL SYSTEM FOR CUTTING AN ANATOMICAL STRUCTURE ACCORDING TO AT LEAST ONE TARGET CUTTING PLANE

FIELD OF THE INVENTION

The invention relates to a robotic system for cutting an anatomical structure of a patient.

BACKGROUND OF THE INVENTION

Total knee arthroplasty typically requires cutting both the femoral epiphysis and tibial epiphysis in order to remove the damaged bone and cartilage and install a knee prosthesis.

To that end, a surgeon has to carry out five or more cuts on the femur and one or more cuts on the tibia by using an oscillating saw through cutting blocks.

FIG. 1 is a schematic perspective view of a knee intended to receive a knee prosthesis including a femoral component FC and a tibial component TC. Generally, the cuts to be made on the femur F are: a distal cut along plane F1, an anterior cut along plane F2, a posterior cut along plane F3, and anterior and posterior chamfers F4, F5 connecting the distal plane and the anterior, respectively posterior, plane. A cut has to be made on the tibia T along plane T1.

In order for the surgeon to carry out cutting along all these planes accurately and in a reduced time, robotic systems have been developed that carry and position the cutting block in accordance with a target plane.

The cutting block generates a certain inaccuracy since the orientation of the saw blade may slightly vary when inserted into a slot of the cutting block, which may change the orientation of the cutting plane relative to the target plane.

In order to improve accuracy of the cutting procedure, it may be desirable to have the saw itself guided by the robotic system.

Two types of robotic systems exist.

On the one hand, large surgical robots with six or more degrees of freedom are very stiff but they are also very cumbersome and expensive. Besides, they have a considerable inertia (especially on the first mobile segment), which is not compatible with real time control of the cutting plane. In addition, these robots are either active or reactive, thus depriving at least partially the user (usually the surgeon) from his/her usual feeling and freedom when accomplishing the surgical gesture.

On the other hand, existing small, lightweight robots that allow the user to freely manipulate the saw cannot be used if they are not rigidly attached to the anatomical structure to be cut.

Roth et al. describe attaching a handheld saw to an end of a robot by means of a planar mechanism. The planar mechanism constrains the saw in a given plane, which is adjusted relative to the patient by the robot based on a preoperative planning and on tracking data of the bone to be cut. However, in this system, only the pose of the connection between the planar mechanism and the last segment of the robot can be accurately determined in the best case. In other words, the pose of the saw relative to the robot cannot be precisely known. Thus, unless the planar mechanism is perfectly stiff, there may be a difference between the real pose of the saw and the expected one, which results in a misalignment of the cutting plane and the target plane. Making the planar mechanism perfectly stiff would be difficult to achieve and would also drastically increase its weight and bulkiness.

BRIEF DESCRIPTION OF THE INVENTION

A goal of the invention is to provide a surgical system intended to guide an end effector to cut an anatomical bony structure of a patient according to at least one target plane, which does not require any invasive attachment to the patient's bone while controlling precisely the position and orientation of the end effector to reach the target plane.

Accordingly, the invention provides a surgical system for cutting an anatomical structure of a patient according to at least one target plane defined in a coordinate system of the anatomical structure, comprising:
(i) a robotic device comprising:
  an end effector,
  an actuation unit having at least three motorized degrees of freedom, configured for adjusting a position and orientation of the end effector (2) relative to each target plane,
  a passive planar mechanism connecting the terminal part of the actuation unit to the end effector;
(ii) a tracker rigidly attached to the end effector,
(iii) a tracking unit configured to determine in real time the pose of the end effector with respect to the coordinate system of the anatomical structure,
(iv) a control unit configured to determine the pose of the end effector with respect to the target plane and to control the actuation unit so as to bring the cutting plane into alignment with the target plane.

Advantageously, the control unit is further configured to implement a control loop comprising the following steps:
(S'1) determining poses of the actuation unit, the end effector and the anatomical structure using localization information provided by the tracking unit;
(S'2) computing a deviation between the cutting plane and the target plane;
if the deviation is less than a threshold, allowing operation of the end effector and returning to step (S'1) to determine a new pose of the actuation unit, end effector and anatomical structure;
if the deviation is greater than or equal to the threshold, projecting (S'3) the cutting plane and the target plane in the coordinate system of the actuation unit,
(S'4) computing a transformation between the plane of the planar mechanism and the cutting plane;
(S'5) updating the target plane with the transformation computed in step (S'4);
(S'6) computing a new attitude of the actuation unit to align the cutting plane with the updated target plane, and determining the movements to be applied by the motors of the actuation unit;
activating the actuation unit (4) to apply said movements.

According to an embodiment, the end effector is a surgical saw comprising a saw blade configured to oscillate within a determined cutting plane. The cutting plane may be parallel to the plane of the planar mechanism. Alternatively, the cutting plane may be orthogonal to the plane of the planar mechanism.

According to an embodiment, the end effector is a burr.

According to an embodiment, the end effector is a laser.

According to an embodiment, the end effector is a high-pressure water jet.

According to an embodiment, the end effector is a scalpel or a lancet adapted for cutting soft tissues.

Advantageously, each degree of freedom of the planar mechanism may be provided with at least one encoder.

According to an embodiment, the planar mechanism comprises a locking system configured to lock each of its degrees of freedom.

According to an embodiment, the planar mechanism comprises at least two linear segments coupled by an articulation axis and said articulation axis is provided with stops configured to limit the range of rotation of the linear segments relative to each other. Said stops may be bulges extending radially outwardly from the articulation axis.

Advantageously, the system may comprise a locking system for locking the end effector to the actuation unit in a rest position.

The locking system preferably comprises a support rigidly coupled to the terminal part of the actuation unit and an intermediate part rigidly attached to the end effector.

According to an embodiment, the end effector locking system is a mechanical locking system. The support may comprise an opening provided with a latch and the intermediate part may comprise a protruding locking member configured to be inserted into the opening and retained by the latch, the support further comprising a button coupled to the latch and configured to release the locking member.

According to another embodiment, the end effector locking system is a magnetic locking system. The support may comprise a magnet or an electromagnet and the intermediate part comprises a magnetic element.

According to an embodiment, the tracking unit is an optical tracking unit.

Alternatively, the tracking unit is an electromagnetic tracking unit.

According to an embodiment, the system further comprises a passive lockable articulated arm holding the robotic device.

BRIEF DESCRIPTION OF THE DRAWINGS

Other features, embodiments and advantages of the invention will be apparent from the detailed description that follows, based on the appended drawings wherein.

DETAILED DESCRIPTION OF EMBODIMENTS OF THE INVENTION

The following description is focused on knee surgery, in particular total knee arthroplasty (TKA), in which case the anatomical structure to be cut is a joint formed of the femur and the tibia.

However, the invention is not limited to this specific application, but can be applied to various applications where there is a need to perform cuts along at least one plane in a bony anatomy. In general, the invention can be used in any surgical intervention requiring at least one osteotomy step. In particular but not limited to, the invention could also be implemented in the following surgical applications: unicompartmental knee arthroplasty (UKA), tibial or femoral osteotomy, patella resurfacing, hallux valgus surgery, hip surgery for cutting the proximal femur, shoulder surgery for cutting the humeral head, spine surgery for correcting deformities and performing an osteotomy of the vertebral body, ankle surgery, maxillofacial surgery.

As will be explained in further detail below, the device is used in a context in which at least one target plane along which the anatomical structure has to be cut is planned before performing the cut(s).

Planning of at least one target plane is performed using patient's pre-operative images (e.g. CT, MRI, Ultrasound images, 2D or 3D X-rays in combination with statistical shape models, PET, etc.) or intra-operative 3D data (e.g. intra-operative CT or CBCT, intra-operative MRI, Ultrasound images, 2D or 3D intra-operative X-ray images, geometric data provided by localizing systems and providing 3D points, clouds of 3D points, surfaces reconstructed from clouds of 3D points, etc.), or both.

Multiple computer-assisted surgery methods exist to register the target plane with a coordinate system attached to the anatomical structure to be cut, using images or geometric patient data collected during surgery.

Typically, intra-operative images or data are used to register pre-operative images in a unique coordinate system attached to the anatomical structure, and usually represented by a tracker that can use any of computer assisted surgery technologies (optical tracker made of reflective markers, optical tracker made of active LEDs, electromagnetic trackers made of coils, combination of inertial sensors, ultrasonic sensors, RFID sensors, etc.).

Using any of these conventional computer-assisted surgery methods results in that the target planes have a known geometric representation in a coordinate system attached to the anatomical structure to be cut, and whose movements are tracked in real-time by a tracking unit as it will be detailed below. Typically, the surgical planning step for total knee surgery results in five target planes defined in a coordinate system attached to a tracker fixed to the femur and one target plane defined in a coordinate system attached to a tracker fixed to the tibia.

Figure 1:
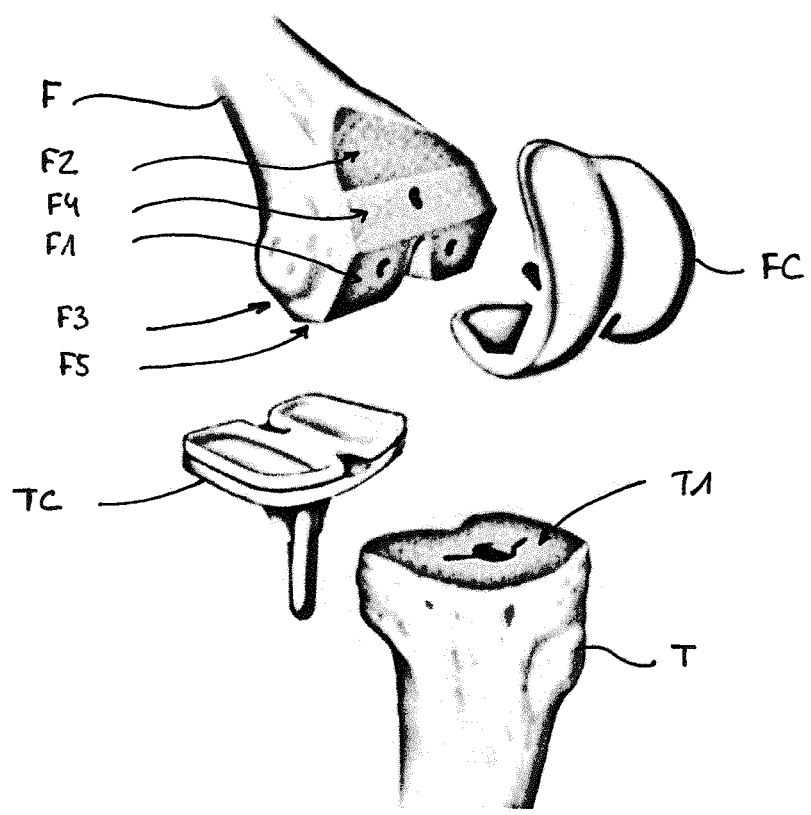
FIG. 1 schematically illustrates the cuts to be made into a femur and a tibia in order to implant a knee prosthesis.
Figure 2:
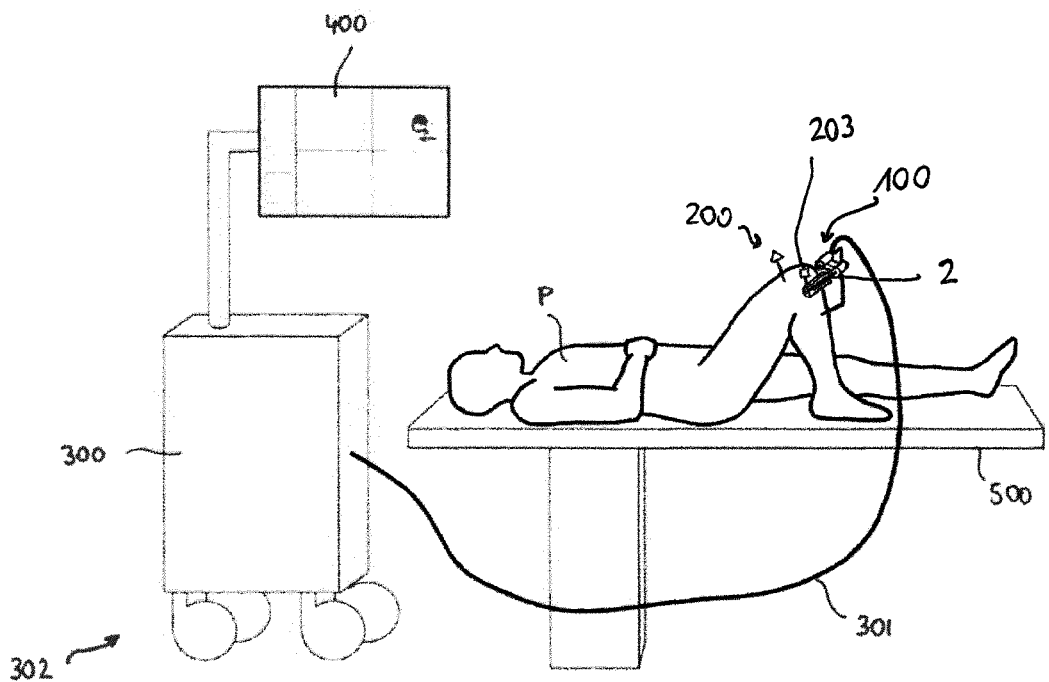
FIG. 2 shows an overview of a surgical system according to the invention.

FIG. 2 shows an overview of a surgical system according to the invention.

A patient P is lying on an operating table 500, e.g. in view of total knee arthroplasty (TKA).

To that end, an end effector, such as a saw 2, which is intended to cut the tibial and femoral bones along at least one target plane—preferably, a plurality of target planes—is used by a user such as a surgeon.

The end effector is held by the robotic device 100 and is constrained in each target plane by an actuation unit 4 (not shown in FIG. 2, but better seen in subsequent drawings).

The robotic device 100 is connected to a control unit 300 that controls the actuation unit.

Said control unit typically comprises power supply, AC/DC converters, motion controllers to power the motors of the actuation unit, fuses, real-time control system interface circuits.

The system also comprises a tracking unit 200, such that the relative pose of the device and the anatomical structure to be cut is tracked in real time and is shared between a real time control unit and a planning system.

At least one coordinate system is attached to the anatomical structure while at least one coordinate system is attached to the end effector and to the robotic device.

The tracking unit measures the relative motions between both coordinate systems in real time. Real time means high frequencies greater than twenty Hertz, preferably in the range of one hundred to five hundred Hertz, with low latency, ideally less than five milliseconds.

The data obtained by the tracking unit are transferred to the control unit 300 via any suitable connection, with wires 301 or wireless, with low latency.

The real-time control unit is able to carry out the proposed real-time control algorithms at a reasonably high frequency with low additional latency.

The real-time control unit computes in real time the position of the end effector with respect to a target plane depending on said measured pose.

In this figure, the connection is represented by a wire 301 but it may instead be wireless if the robotic device is battery-powered.

The control unit and tracking unit may be arranged in a cart 302 that can be moved in the operating room. They can be also mounted on separate carts, articulated holding arms, lighting systems, or the tracking unit can be also mounted directly on the anatomical structure or on some parts attached to the robotic device. For example, the end effector can rigidly support an electromagnetic emitter while electromagnetic sensors can be attached to the anatomical structure.

The system may also comprise a visual user interface 400 that is intended to display feedback information to a user and enable system configuration by the user. The feedback information may comprise:

- indication about a deviation (distance and/or angle) between the cutting plane and the target plane, before the anatomical structure is cut;
- indication about whether the target plane can be achieved with the current position of the robotic device;
- directions to reposition the actuation unit with respect to the anatomical structure to be cut in order to allow the actuation unit to align the cutting plane with the target plane;
- indication about a deviation (distance and/or angle) between the cutting plane and the target plane, while the anatomical structure is being cut;

Said user interface 400 may advantageously comprise a screen, which may be located on a cart in the operating room, e.g. on the same cart 302 as the control unit and tracking unit, or on a separate cart, or attached to the walls or the ceiling of the operating room.

In addition to or instead of said screen, the user interface may comprise an indicator that is arranged on the robotic device itself to provide information to the user. Said indicator can be made of LEDs arranged to indicate arrows, numbers or letters, or a miniature display.

A surgical system wherein the control unit, tracking unit and/or user interface are embedded in the robotic device itself would still be within the scope of the invention, provided that the embedded units are powered by a sufficiently powerful power supply or battery and that their size and weight do not hinder the manipulation of the robotic device by the user. For example, micro cameras can be attached to the base of the actuation unit and markers can be attached to the anatomical structure and to the end effector.

According to an embodiment, the end effector is a surgical saw attached to the actuation unit using a planar mechanism. The saw 2 comprises a casing 23 and a saw blade 22 that oscillates in a determined plane (called "cutting plane") relative to the casing 23 (see in particular FIGS. 6-9). Thus, the saw blade can be operated to cut the anatomical structure according to a target plane without requiring any cutting block, provided that the actuation unit 4 constrains the saw in the target plane in real time. Usually, the cutting plane is parallel to the longitudinal axis of the casing and the saw blade oscillates on both sides of this axis; such a saw is known in the medical field as a "sagittal saw". The casing is usually positioned relative to the planar mechanism so that the cutting plane is parallel to the plane of the planar mechanism.

According to an embodiment, the saw blade moves back and forth along the longitudinal axis of the casing; such a saw is known in the medical field as a «reciprocating saw». The casing is usually positioned relative to the planar mechanism so that the cutting plane is orthogonal to the plane of the planar mechanism.

According to an embodiment (see FIG. 15), the end effector is a burr 2'. Indeed, especially if the burr tip is small (e.g. with a diameter of the order of three mm), the operation of the burr constrained in a cutting plane allows performing a planar cut. The burr tip can be spherical or cylindrical. Typically a cylindrical shape burr tip with a three mm diameter constrained by the planar mechanism to remain in a plane parallel to the cylinder axis will be rigid enough to make large cuts and small enough to perform fast cutting.

According to an embodiment (not illustrated), the end effector is a laser with a system to control the depth of penetration of the laser to avoid damaging soft tissues behind the bone.

According to another embodiment (not illustrated), the end effector can be a high-pressure water jet or any other device that creates cuts in an anatomical structure.

According to another embodiment, for cutting soft tissues, the end effector can be a scalpel or any electrically activated device such as a lancet or an ultrasonic cutter.

In the drawings that are described below, the end effector is usually a saw, without any intended limitation of the invention.

The actuation unit comprises at least three motorized degrees of freedom. Possibly, if there is redundancy, the actuation unit may comprise more than six motorized degrees of freedom.

The actuation unit may have a serial architecture, a parallel architecture or a mixed serial and parallel architecture.

According to an embodiment, the actuation unit 4 has a serial architecture made of a plurality of mobile segments, comprising from three to six motorized degrees of freedom, at least two of which being rotational degrees of freedom orthogonal to each other. In the present text, the term "axis"

designates the geometric rotation or translation axis corresponding to said degree of freedom. Besides, the axes and segments are numbered with increasing numbers starting from the base (i.e. the part of the robotic device that remains stationary while the robotic device works) and towards the terminal part that is connected to the end effector; this type of numbering is conventional for serial robotic architectures.

In some embodiments, the actuation unit has three motorized rotational degrees of freedom for adjusting the position and orientation of the cutting plane relative to each target plane.

In other embodiments, the actuation unit has two motorized rotational degrees of freedom and one or two motorized translational degrees of freedom.

According to another embodiment, the actuation unit presents a parallel architecture comprising a base and a platform selectively orientable relative to the base. To that end, the platform is linked to the base by a plurality of links each providing a degree of freedom in rotation, and if appropriate, also in translation. Various embodiments of parallel architecture exist, such as hexapods, Hayward wrists, Agrawal wrists, Gosselin's agile eyes, Tesar wrists, Cheng wrists, etc.

Depending on the architecture of the actuation unit, the components of the actuation unit may be integrated in an optimal way such that the robotic device remains as compact and light as possible while remaining strong enough to be able to hold the planar articulation and the end effector, as well as resisting to some normal pressure applied by the user when he/she manipulates the end effector. This may be especially the case if the actuation unit has at most five motorized degrees of freedom. In some embodiments, the architecture of the actuation unit may enable additional movements—which can be motorized or not—within the cutting plane. However, it is not excluded to obtain such a capacity with an architecture having six degrees of freedom or more.

Figure 3:
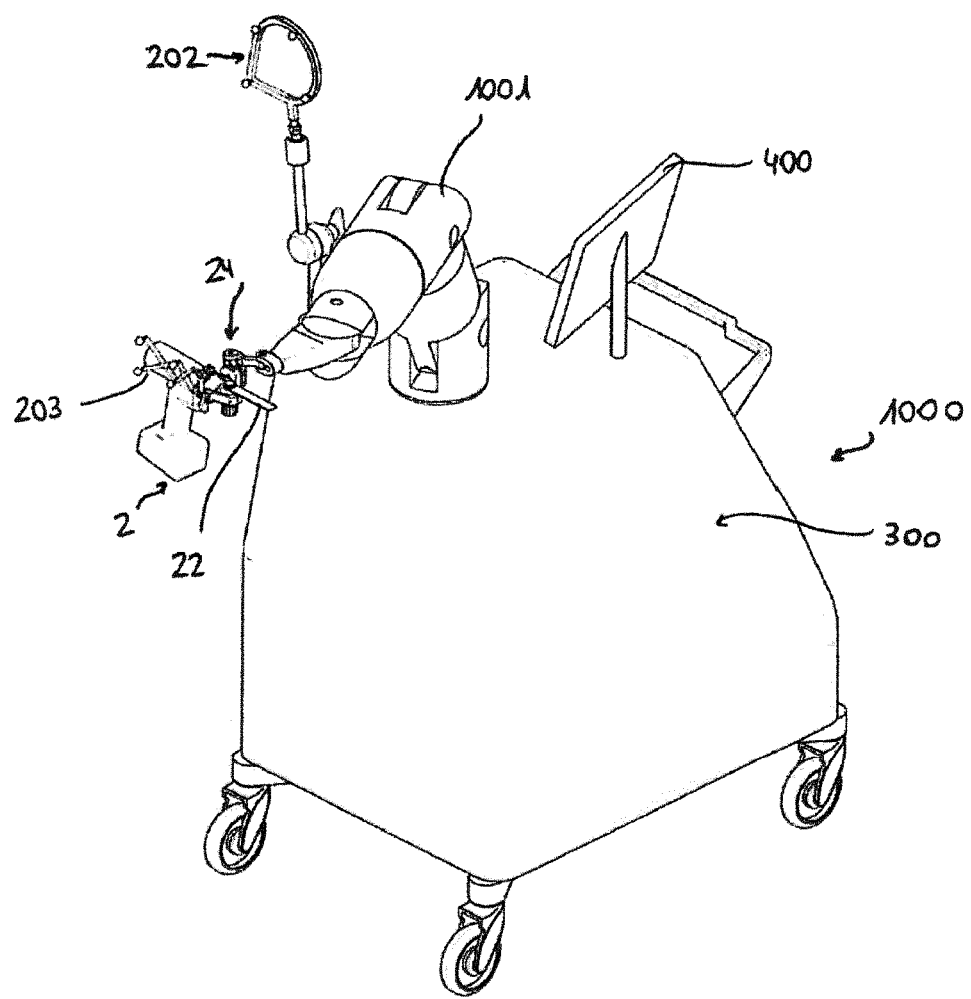
FIG. 3 is a perspective view of a robotic device according to a first embodiment of the invention.

In some embodiments the robotic device may not be as compact as in the embodiments described above, and the robotic device can thus rather be assimilated as a large surgical robot. As shown in FIG. 3, the robot 1000 comprises an arm 1001 having a serial architecture comprising six motorized degrees of freedom, a planar mechanism 24 connecting the last segment of the arm to an end effector 2. The robot is used with a tracking unit configured to determine in real time the pose of the cutting plane with respect to the coordinate system of the anatomical structure of the patient. The tracking unit comprises at least one tracker (not shown) configured to be attached to the anatomical structure, a tracker 202 attached to a segment of the arm of the robot and a tracker 203 attached to the end effector 2. Indeed, since the planar mechanism is very close to the surgical field, it has to remain compact and thus prone to bending under efforts exerted by the surgeon when cutting. Even if the large surgical robot is accurate, it cannot itself compensate for such bending of the planar mechanism. However, using a tracker on the end effector and implementing the above-mentioned compensation method allows overcoming this problem.

As compared to such a large surgical robot, a compact actuation unit presents a lower inertia—especially according to the first axis—and thus a greater responsiveness required in particular to compensate for bone motion in real time.

The robotic device may be held by a holding arm, especially if the robotic device is compact and lightweight, whatever the number of its degrees of freedom. The holding arm does not require any invasive action onto the patient while fully supporting the weight of the robotic device.

Such a holding arm supports the actuation unit and is suited to be connected to a mechanical support such as an operating table, a leg holder or mounted on a mobile cart which wheels can be blocked. A leg holder is an adjustable mechanism configured to maintain the leg in a given flexed position when the patient lies on the operating table.

The holding arm is made of several articulated segments using ball-and-socket joints, rotational and/or translational joints.

The holding arm is lockable, either manually by a knob (mechanical locking system) or actively by a dedicated actuator of a locking system. The locking system may be an electrical system, a piezoelectric system, a hydraulic system, a pneumatic system or a combination of such systems (e.g. a hydraulic cylinder driven by an electric motor). For example, company SMITH & NEPHEW sells a passive holding arm, actively lockable, named SPIDER™. The actuator can be a button, a foot switch, a remote button, etc. To manipulate the robotic device, the user has to maintain the actuator activated until the desired pose of the robotic device has been achieved.

The holding arm supports the weight of the robotic device and maintains it in a rough positioning relative to the anatomical structure to be treated. It limits the movements of the user when operating the device—and, in advantageous embodiments, also damps movements of the user and/or the patient, vibrations of the end effector and reaction forces caused by movements of the actuation unit.

According to an embodiment, the holding arm is passive.

Advantageously, the holding arm may be braked progressively depending on the distance between the robotic device and a target position of the robotic device relative to a tracker fixed to the patient. For example, the braking force may be inversely proportional to the distance of the robotic device to its target position. Alternatively, one or several concentric volumes (e.g. cubes or spheres) may be defined around the target position of the robotic device. The braking force may adjust depending on the presence of the robotic device in one of said volumes. Thus, when the robotic device is close to the target position, the holding arm is braked and the user may receive a force-feedback information. Alternatively, feedback information may be provided in the form of a light or acoustic signal. For example, a variable flash frequency and/or intensity of a light signal may indicate the distance between the robotic device and its target position. Similarly, a variable frequency, repeat speed and/or amplitude of an acoustic signal may indicate such a distance. In any case, the braking is not full, so that the user is always able to manipulate the robotic device until its final desired position. The holding arm is then locked upon an action from the user (e.g. by operating the actuator, e.g. releasing or pushing a button). If the user wants to move the robotic device again, he/she has to operate the actuator again, which frees the holding arm—possibly with a braking force as described above. If a new target position of the robotic device is defined, new braking volumes are defined, and the braking is adjusted based on said new volumes.

In an embodiment, the holding arm is equipped with weights to counterbalance the weight of the control unit, as it is commonly used for carrying and placing microscopes in the surgical field for example.

In an embodiment, the holding arm has a vertical translation with a spring mechanism to compensate for the weight of the global system, then it has a serial architecture with a large planar structure made of three parallel and vertical axes. Each axis is equipped with a locking system.

Figure 4:
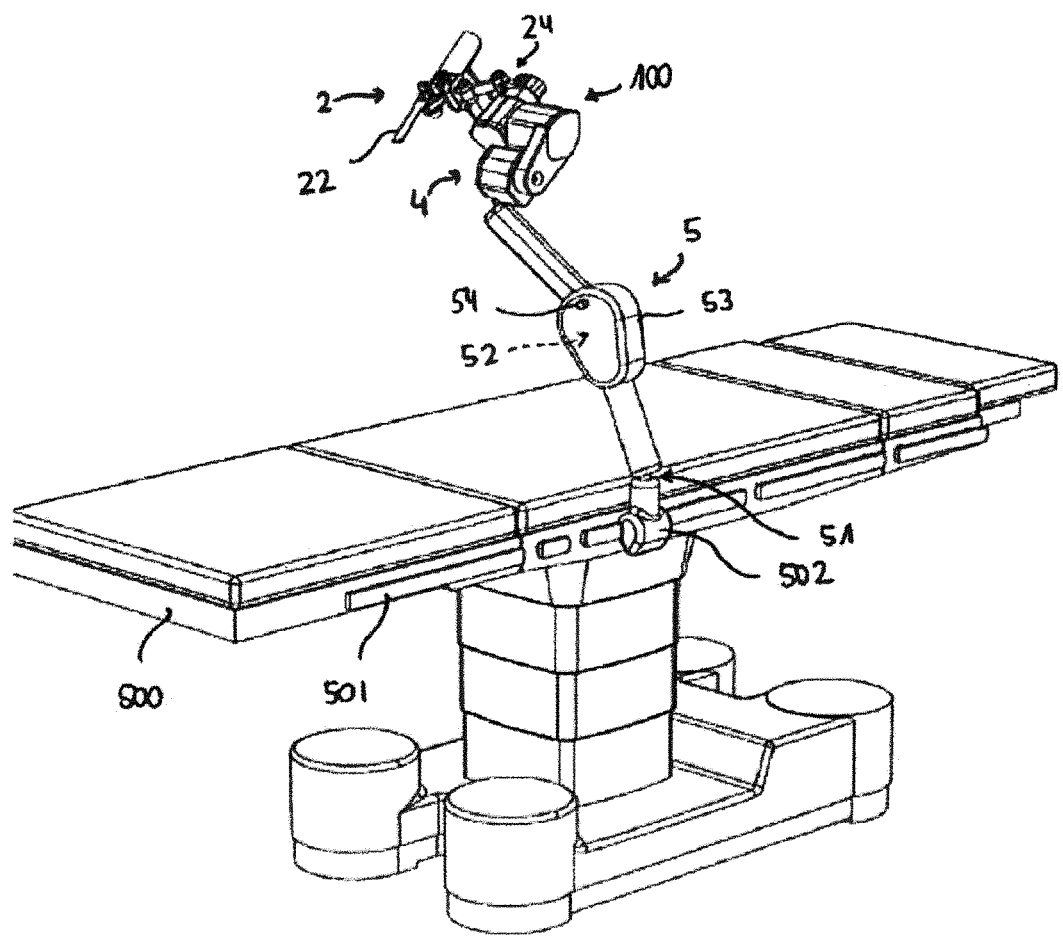
FIG. 4 is a perspective view of a robotic device according to a second embodiment of the invention.

FIG. 4 illustrates an embodiment of the holding arm 5, which is fixed to a rail 501 of the operating table 500 by a clamp 502. The holding arm is formed of the following kinematic links, in a sequence starting from the clamp: a pivot link 51 and a ball joint 52. The central module 53 is provided with an actuator 54 that allows unlocking the holding arm when pushed. Alternatively, such an actuator could be arranged on a higher part of the holding arm so as to manipulate the arm and the robotic device easily in case the user wants to change the position of the robotic device relative to the anatomical structure.

Figure 5:
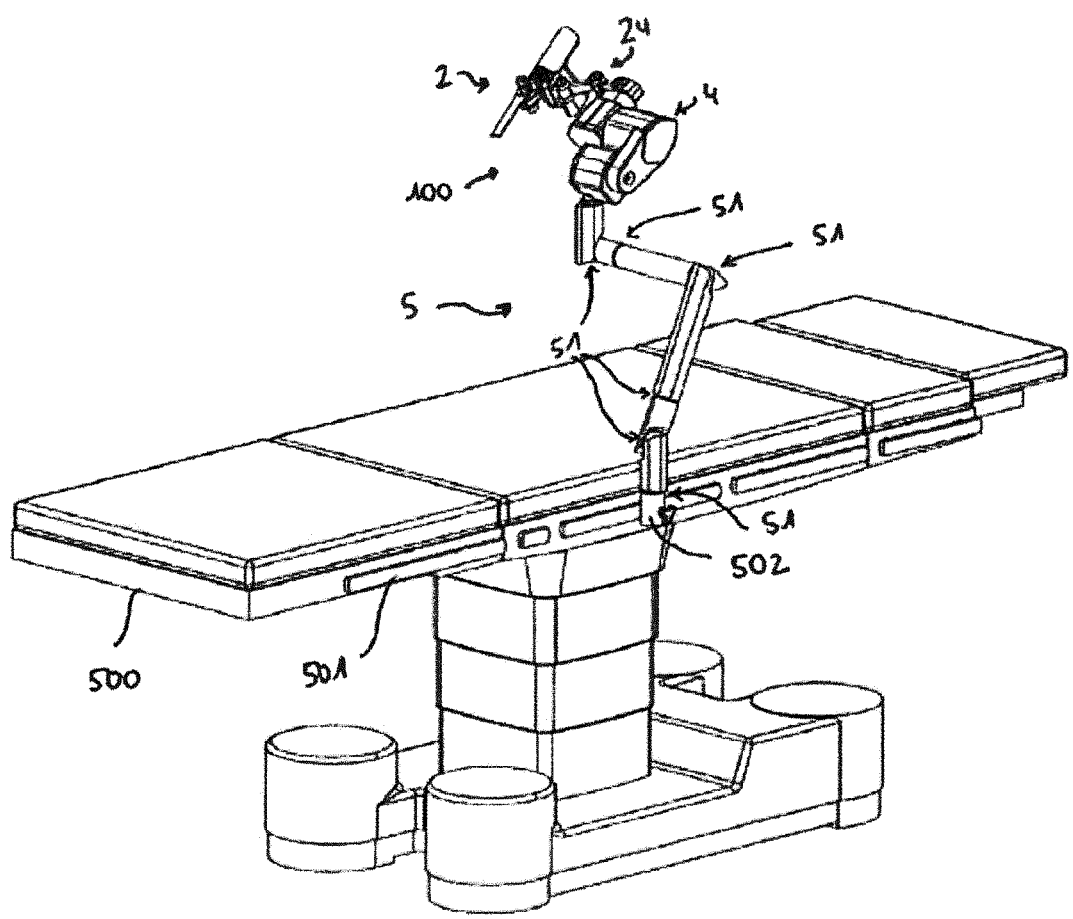
FIG. 5 is a perspective view of a robotic device according to a third embodiment of the invention.

FIG. 5 illustrates another embodiment of the holding arm 5, which is fixed to a rail of the operating table 500 by a clamp 501. The holding arm is formed of six pivot links 51. The holding arm may be locked by an actuator (not shown).

Preferably, the connection between the holding arm and the actuation unit is as close as possible to the first segment of the actuation unit or to the center of gravity of the robotic device in order to minimize any lever-arm effect. The part of the actuation unit that is attached to the holding arm is called the base of the robotic device.

If the actuation unit has a serial architecture, the first segment of the actuation unit may be fixed relative to the holding arm. In such case, the second segment of the actuation unit is necessarily mobile relative to the first segment. This architecture is advantageous in that it minimizes the weight of the moving components of the actuation unit. As a result, the robotic device may be more responsive, which is favorable to real time control of the cutting plane. Alternatively, the first segment of the actuation unit may be mobile relative to the holding arm. In such case, the first and second segments are preferably embedded in a single housing.

If the actuation unit has a parallel architecture, the base of the actuation unit may be fixed relative to the holding arm.

As it will be explained in more details below, the actuation unit 4 is controlled by the control unit 300. The control unit may be integrated in the robotic device, or remote from the robotic device.

The end effector is coupled to the actuation unit by a planar mechanism designated under reference 24 throughout the set of drawings, the planar mechanism being configured to constrain the movement of the end effector within the cutting plane.

Advantageously, the end effector can be decoupled from the planar mechanism. Preferably, especially in the case where the end effector is not intended to receive a tracker, the attachment means for the end effector provides reproducible fixation.

Several different architectures exist to implement a planar mechanism. For example, the planar mechanism can be made of only one rotation axis and then one translation axis that carries the end effector along its longitudinal direction. Otherwise, the planar mechanism can be made of two or more rotation axes. Alternatively, the planar mechanism can be made of two orthogonal translation axes and then a rotational axis. According to another embodiment, the planar mechanism can be a slider in the form of an arch, including a rotation axis, and then a translation axis that carries the end effector.

FIGS. 6-9 illustrate various non-limitative embodiments of the planar mechanism. Although the actuation unit is represented with a serial architecture and the end effector is represented as a saw, the invention could be implemented with any other type of actuation unit or end effector. The arrows indicate the degrees of freedom of the planar mechanism in each embodiment.

Figure 6:
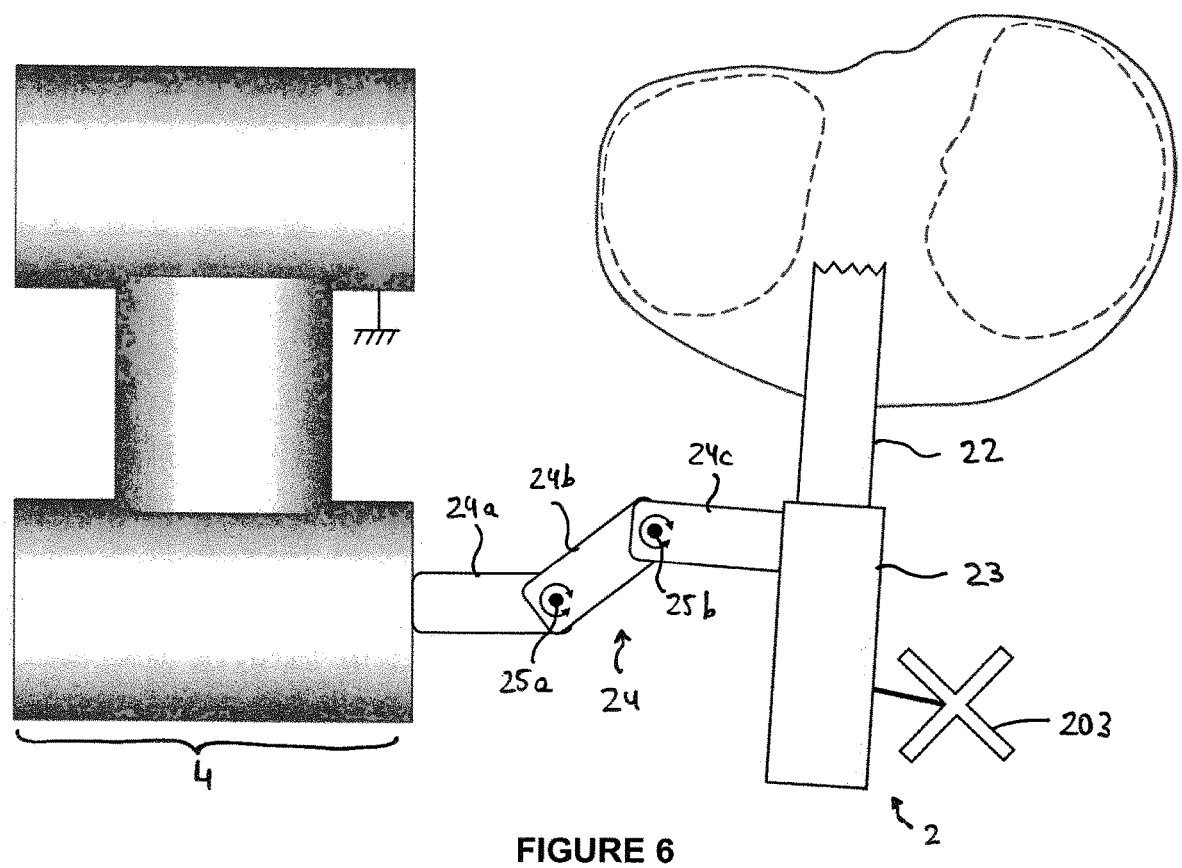
FIGS. 6-9 show various embodiments of the planar mechanism connecting the end effector to the actuation unit.

FIG. 6 illustrates a planar mechanism 24 comprising three linear segments 24a, 24b, 24c articulated about two rotation axes 25a, 25b that are orthogonal to the segments. The first segment 24a is rigidly coupled to the actuation unit and the third segment is rigidly coupled to the end effector.

Figure 7:
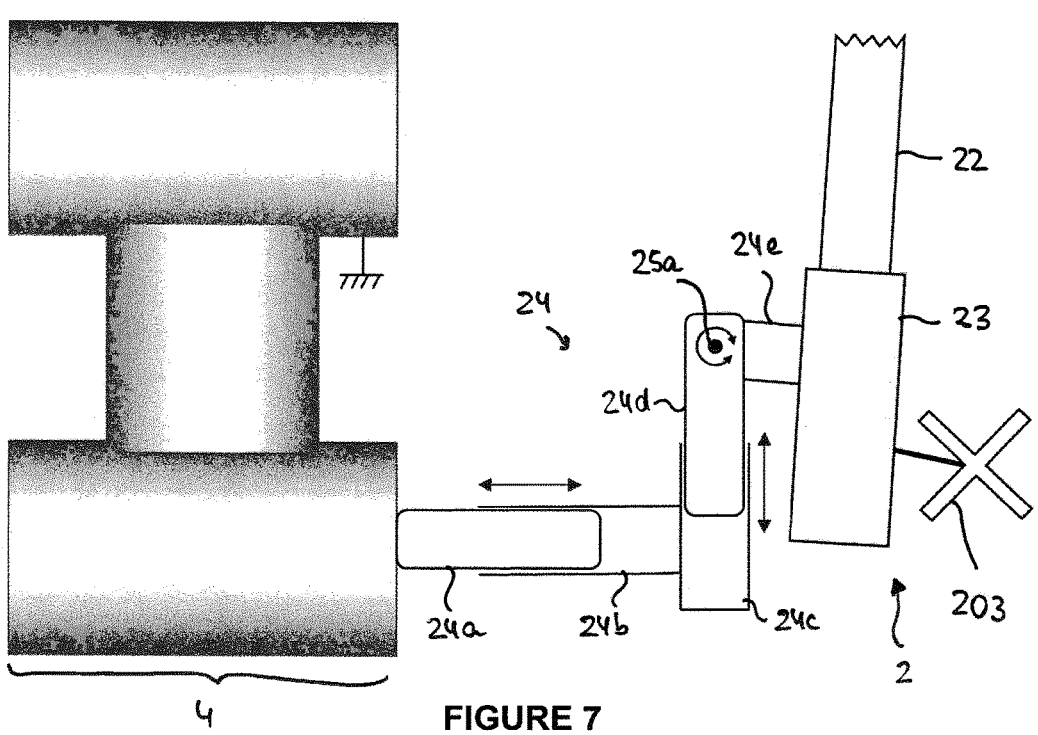

FIG. 7 illustrates a planar mechanism 24 comprising five linear segments 24a-24e. The first and second segments 24a, 24b are in sliding engagement relative to each other, as well as the third and fourth segments 24c, 24d. The second and third segments 24b, 24c are rigidly coupled to each other and may form a single piece. The fourth and fifth segments 24d, 24e are articulated about a rotation axis 25a that is orthogonal to the segments. The first segment 24a is rigidly coupled to the actuation unit and the fifth segment 24e is rigidly coupled to the end effector.

Figure 8:
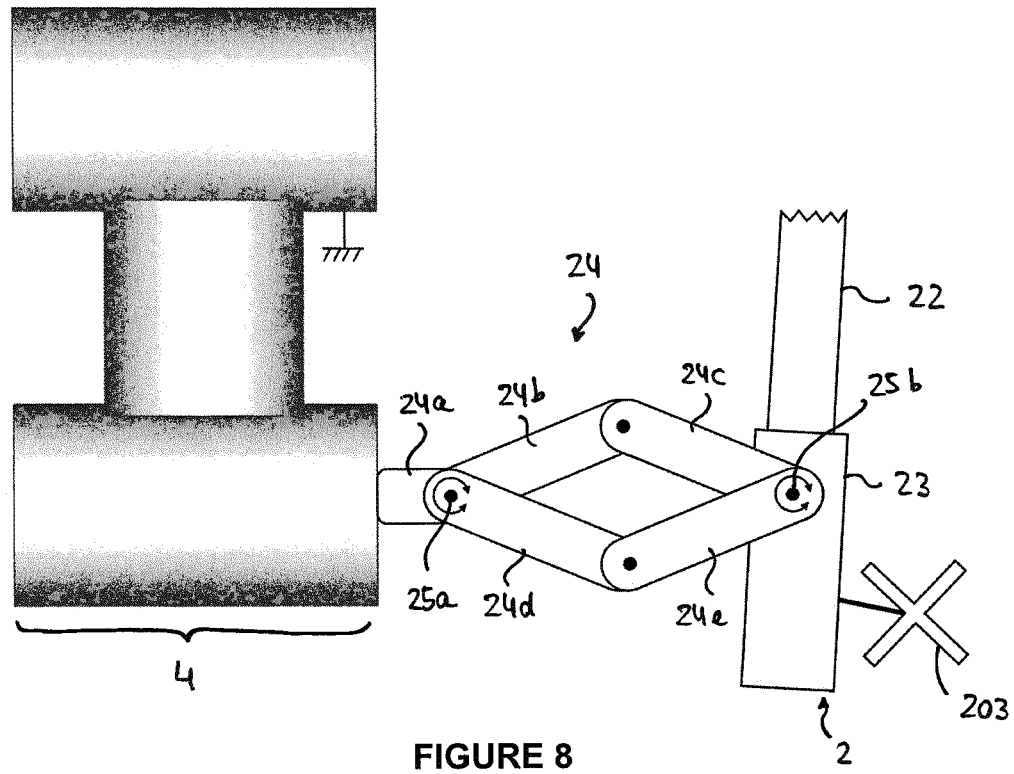

FIG. 8 illustrates a planar mechanism 24 comprising five linear segments 24a-24e. The first segment 24a is rigidly coupled to the actuation unit 4. Two pairs of segments (respectively 24b-24c and 24d-24e) are connected to form a parallelogram. The segments 24b, 24d are articulated on the first segment 24a by a rotation axis 24a that is orthogonal to the segments. The segments 24c, 24e are coupled to the end effector by a rotation axis 25b. The segments of each pair 24b-24c and 24d-24e are articulated about a respective axis that is orthogonal to said segments.

Figure 9:
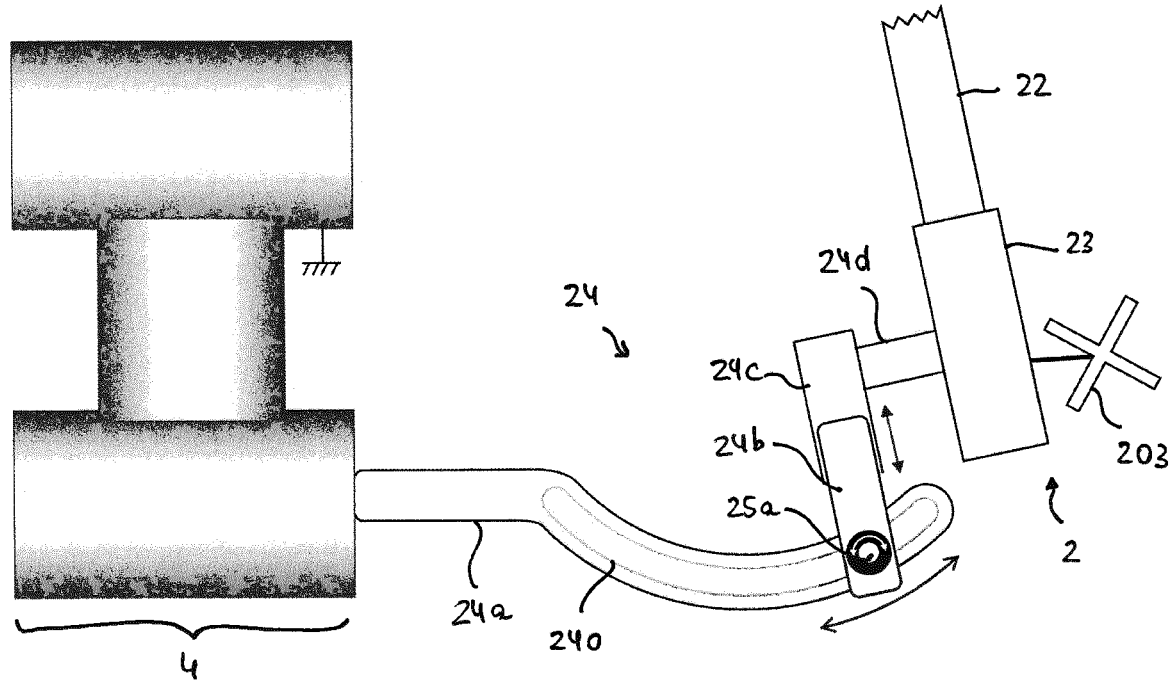

FIG. 9 illustrates a planar mechanism 24 comprising a first segment 24a including a curved slot 240, a second linear segment 24b coupled to the first segment 24a via an axis 25a orthogonal to said segments. The axis 25a is able to slide within the curved slot 240, and the second segment 24b is rotatable relative to the axis 25a. A third linear segment 24c is in sliding engagement with the second segment, and rigidly connected to a fourth linear segment 24d that carries the end effector. The third and fourth linear segments 24c, 24b may form a single piece.

Figure 10A:
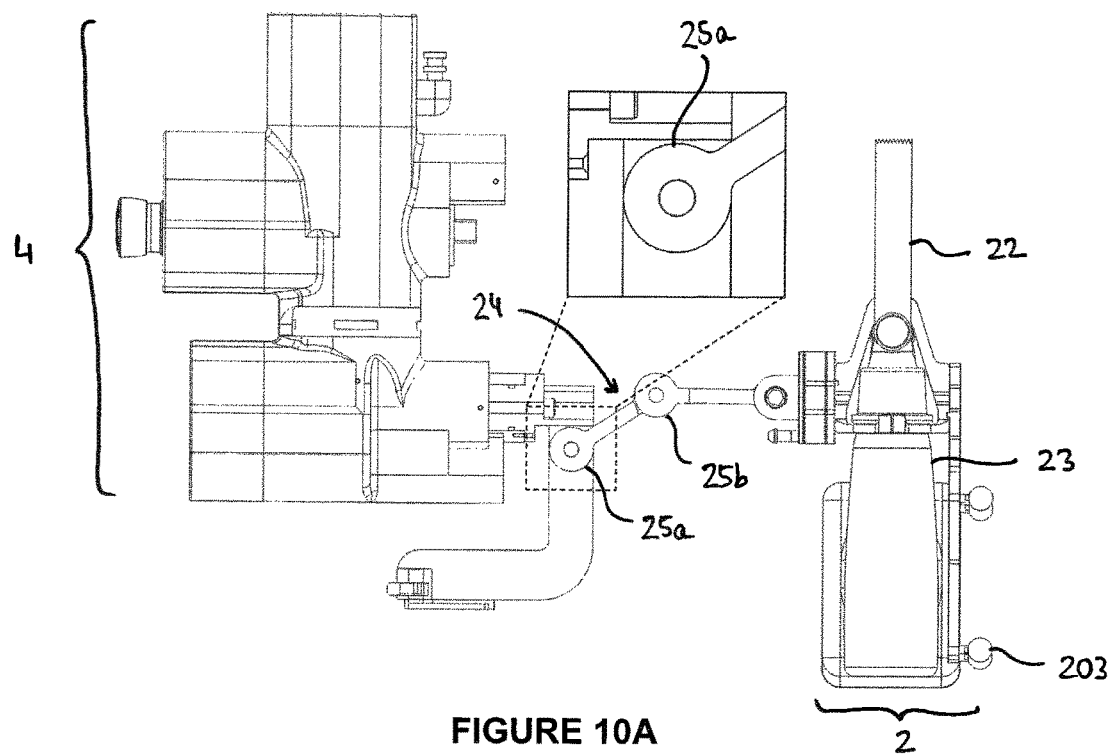
FIGS. 10A and 10B illustrate an embodiment of the robotic device without limitation to the range of rotation of the segments of the planar mechanism.
Figure 10B:
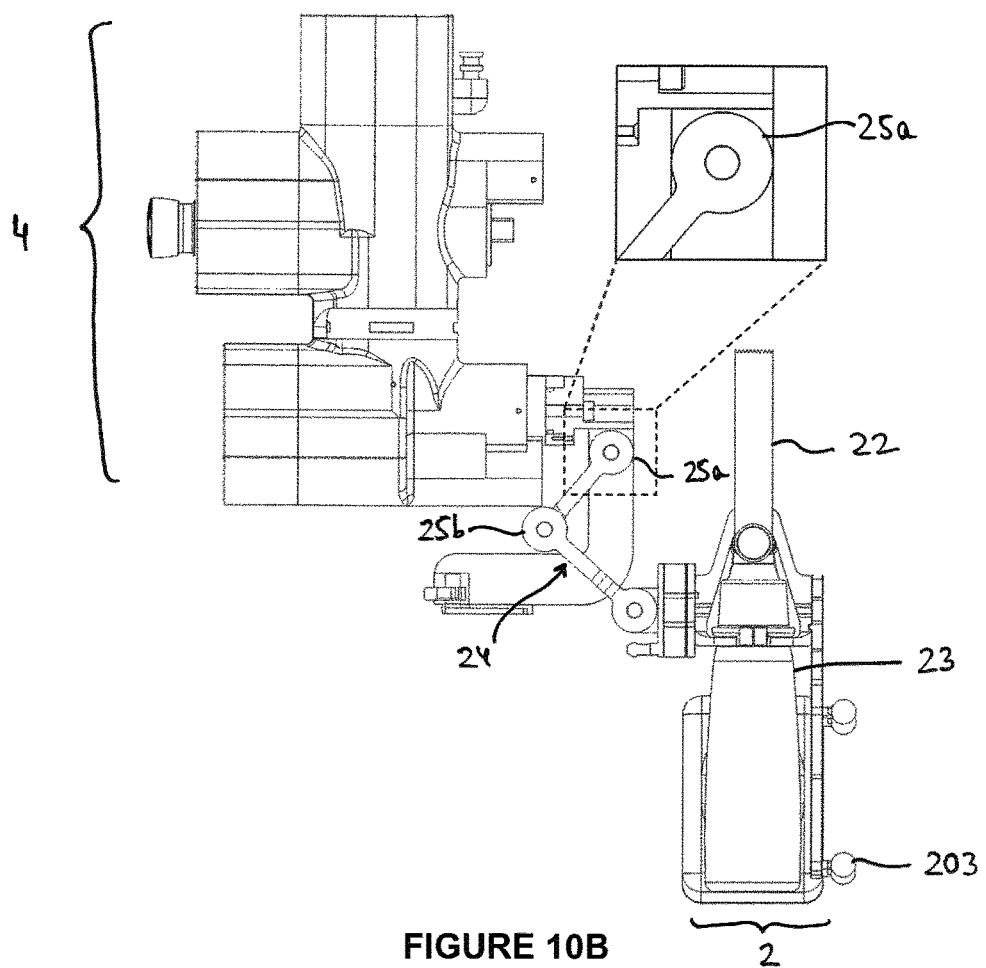

FIGS. 10A and 10B illustrate an embodiment of the robotic device, wherein the planar mechanism is of the type illustrated in FIG. 6. In this embodiment, the articulation axes 25a, 25b have a circular shape, which does not restrict the range of rotation of each linear segment relative to another one. This may result in some unsuitable configurations of the planar mechanism that may limit or even hinder some movements of the end effector 2 (see FIG. 10A), and/or that may cause the end effector 2 to collide with the actuation unit 4 (see FIG. 10B).

Figure 11A:
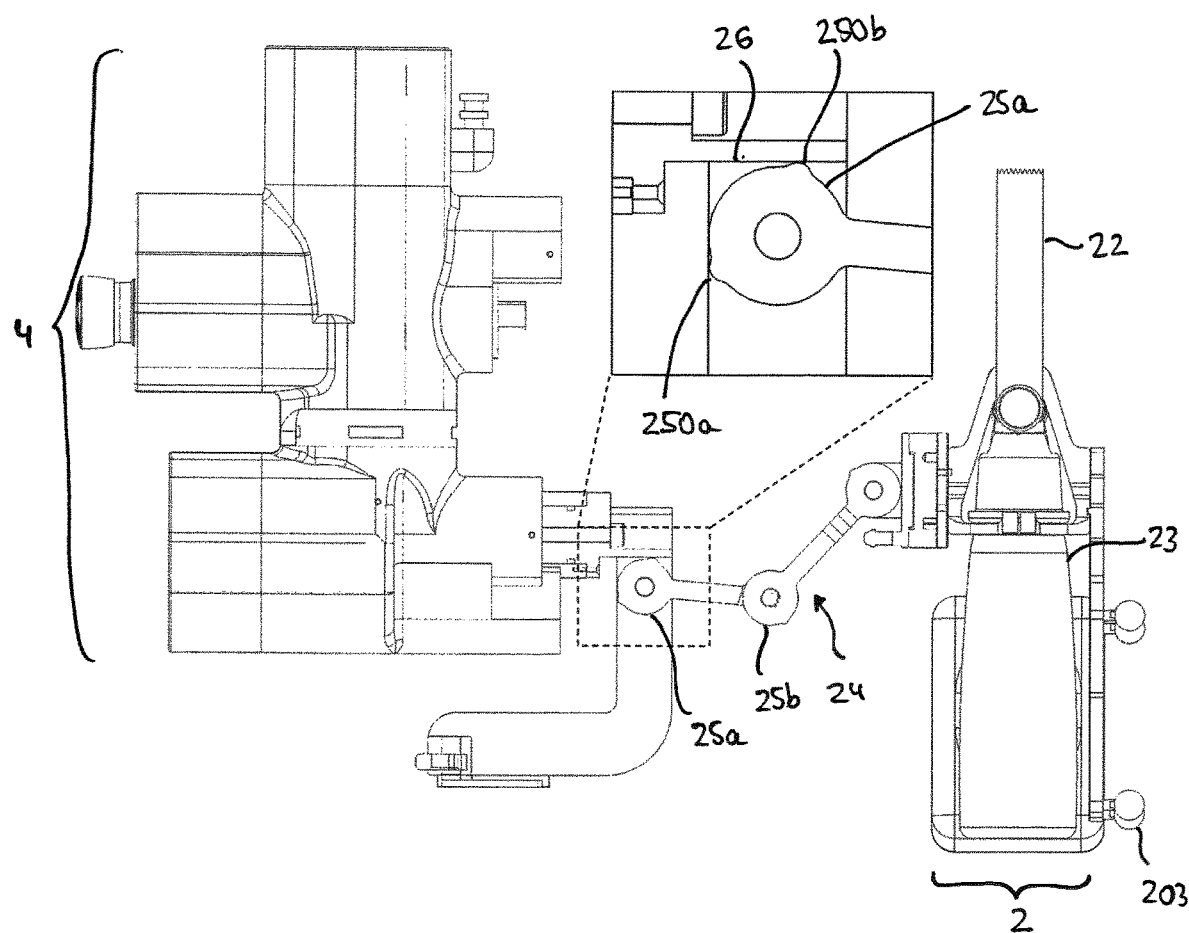
FIGS. 11A and 11B illustrate an embodiment of the robotic device with stops configured to limit the range of rotation of the segments of the planar mechanism.
Figure 11B:
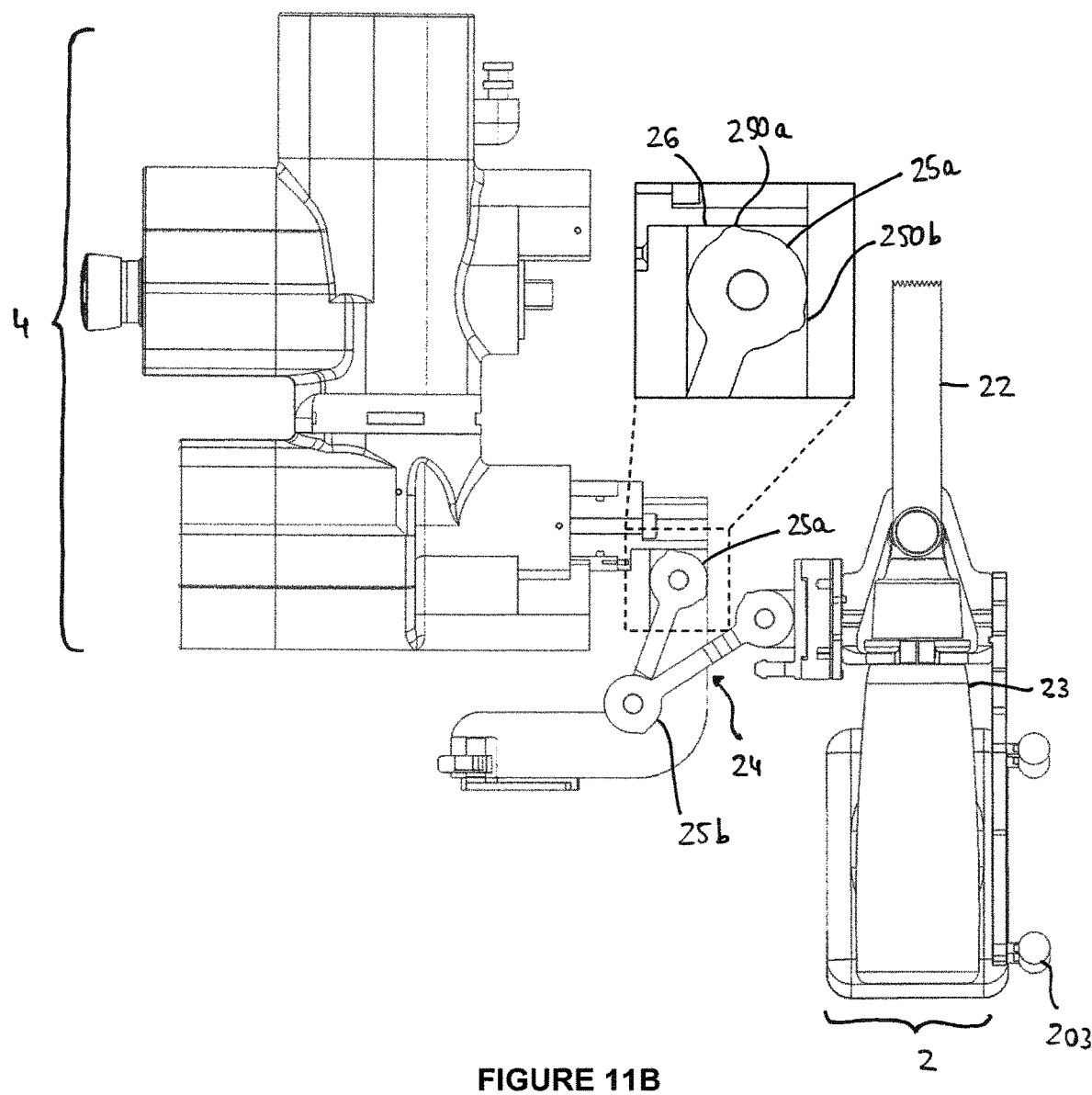

FIGS. 11A and 11B illustrate an alternative embodiment of the robotic device comprising stops arranged on at least one axis 25a of the planar mechanism 24 to limit the angle of rotation of the segments relative to each other. Said stops may consist in bulges 250a, 250b extending radially on the circumference of the articulations axes. Said bulges are located in a selected position so as to interfere with a complementary part 26 when an extreme position has been reached, thereby preventing any further rotation of the linear segment. In FIG. 11A, as compared to FIG. 10A, the stop 250a that is arranged on the first axis 25a on the side of the actuation unit prevents the second axis 25b from being moved towards the top of the figure. In FIG. 11B, as compared to FIG. 10B, the other stop 250b that is arranged on the first axis 25a prevents the end effector 2 from being brought in contact with the actuation unit 4. The stop 250b also allows the user to find more easily the locking position of the end effector, that will be described with reference to FIGS. 12A-12B and 13A-13B.

The planar mechanism is passive, meaning that the mechanism is not motorized and can be freely manipulated by the user. One advantage of such a passive mechanism is to preserve all the perceptions of the user when the saw is manipulated in the bone. Thanks to the planar mechanism, the user remains free to move the cutting tool within the target plane, thereby enjoying his/her usual feeling when accomplishing the surgical gesture. This also provides for a greater safety of use of the robotic device, since the user's intervention is always required to perform the cut. For example, surgeons are used to freely manipulate a saw in a cutting block and to detect when the saw blade has reached the back of the bone by sensing changes in the bone resistance, and this perception is fully preserved with a passive planar mechanism that has very low friction at its joints. In this respect, the planar mechanism is advantageously provided with bearings that provide such a low friction for the various degrees of freedom.

The planar mechanism may advantageously be made of lightweight and compact components so as to limit its bulkiness and thus to allow placing the end effector in any desired pose relative to the patient. As will be explained in more detail below, even if such a lightweight structure lacks stiffness, the invention provides for a control unit that is configured to implement a control loop that allows compensating for any offset between the real pose of the end effector and its theoretical one (i.e. the pose assuming that the planar mechanism is perfectly stiff and always maintaining the end effector within the intended plane). The control loop uses a continuous tracking of the end effector.

In addition, the planar mechanism may comprise a locking system for locking each of its degrees of freedom once a desired configuration has been achieved.

As an alternative to the locking system of the planar mechanism, the robotic device may advantageously comprise a locking system for locking the end effector in a fixed position relative to the actuation unit when the robotic device has to move to a new position.

Various locking systems may be used (mechanical, magnetic, etc.).

Figure 12A:
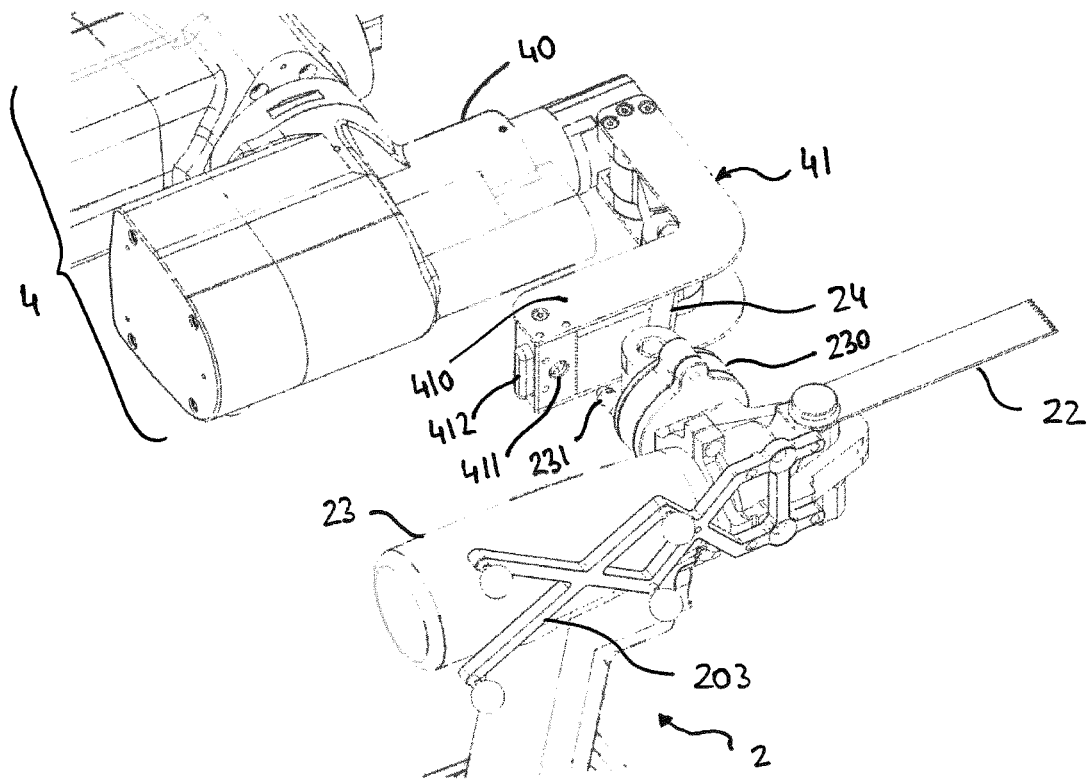
FIGS. 12A and 12B illustrate an embodiment of a mechanical locking system for securing the end effector to the actuation unit, respectively in unlocked and locked configuration.
Figure 12B:
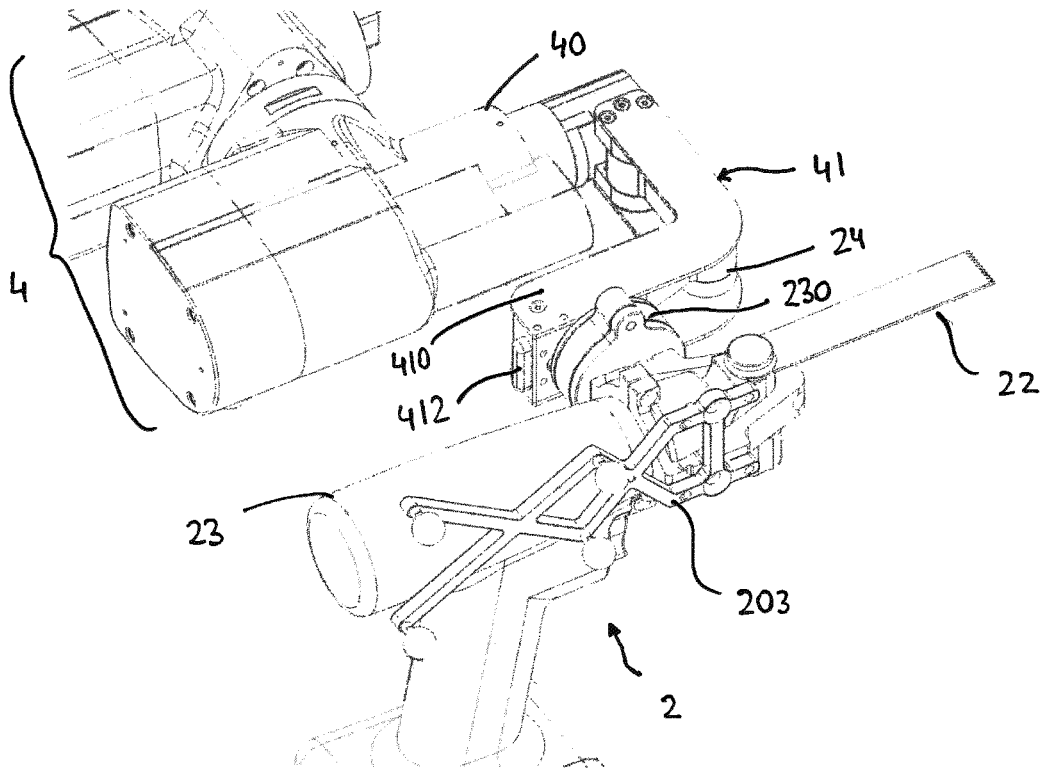

FIGS. 12A and 12B illustrate an embodiment of a mechanical locking system, respectively in unlocked and locked (rest) position. The terminal part 40 of the actuation unit 4 is rigidly attached to a curved support 41 into which the planar mechanism 24 is arranged. The end effector 2 is intended to face a part 410 of the curved support 41 in its rest position. Said part 410 of the curved support 41 comprises an opening 411 for receiving a locking member 231 protruding from an intermediate part 230 attached to the end effector 2, and a latch (not shown) for maintaining the locking member 231 fixed to the curved support 41 once it has been inserted into the opening 411. The curved support 41 also comprises a button 412 coupled to the latch to release the locking member 231 when said button 412 is pressed by a user.

Figure 13A:
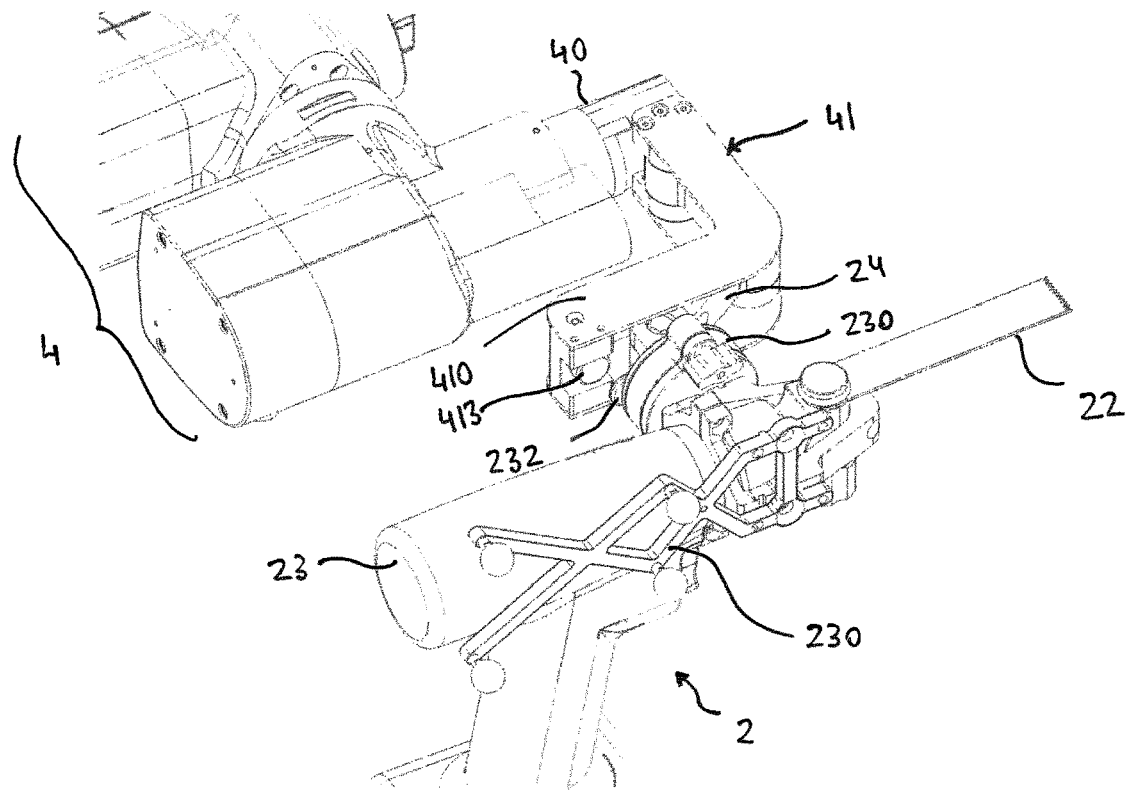
FIGS. 13A and 13B illustrate an embodiment of a magnetic locking system for securing the end effector to the actuation unit, respectively in unlocked and locked configuration.
Figure 13B:
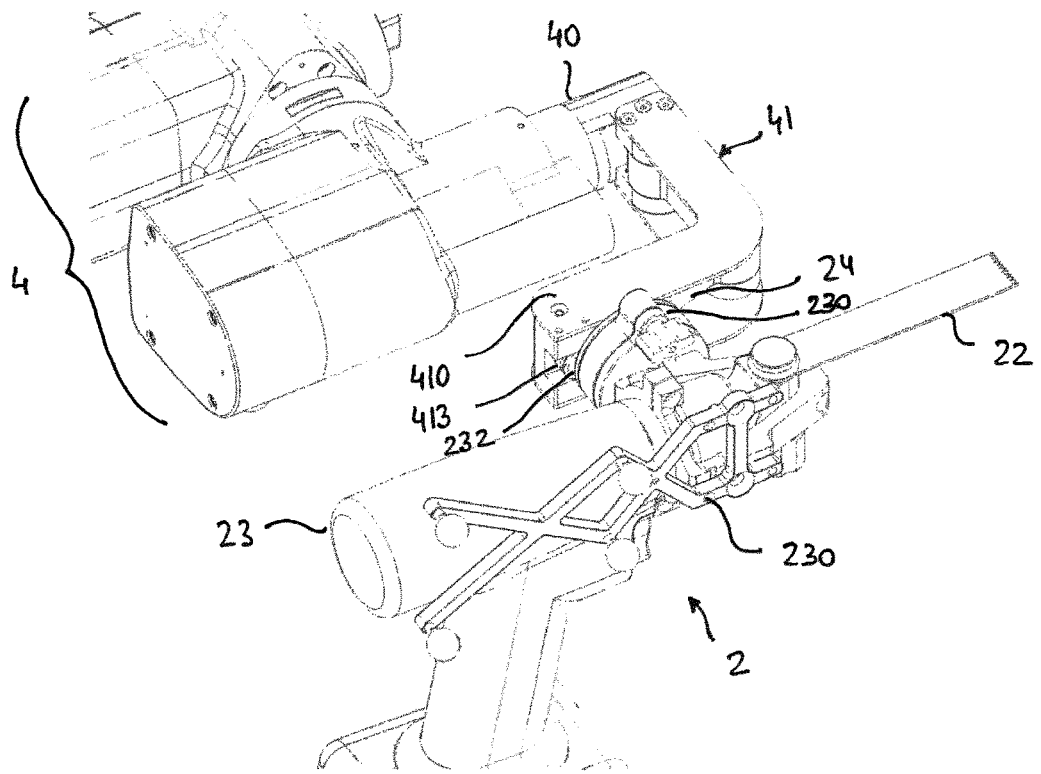

FIGS. 13A and 13B illustrate an embodiment of a magnetic locking system, respectively in unlocked and locked (rest) position. The terminal part 40 of the actuation 4 unit is rigidly attached to a curved support 41 into which the planar mechanism 24 is arranged. The end effector 2 is intended to face a part 410 of the curved support 41 in its rest position. Said part 410 of the curved support 41 comprises a magnet 413 configured to retain a corresponding magnetic element 232 on the end effector (or on a part 230 attached to the end effector). The magnetic force is selected to be high enough to strongly maintain the end effector onto the support, while allowing a user to release the end effector in a smooth way.

Of course, the invention could be implemented with any other configuration of such a locking system. For example, the magnet may be replaced by an electromagnet.

One advantage of the above-described locking system of the planar mechanism or of the end effector is that the end effector is maintained fixed relative to the terminal component of the actuation unit when the robotic device is being moved, which avoids any undesired movement of the end effector during this movement, which could cause the end effector to hit the patient, the user or an element of the operating room. In addition, with the locking system of the end effector, the actuation unit and end effector form a compact assembly, which is easier to move to a new desired position.

The locking unit may be provided with detectors allowing detecting whether the end effector is locked into the rest position or not.

The control unit may be configured to allow movement of the actuation unit only if such a locking into the rest position is detected.

It is to be noted that, since the end effector is equipped with a tracker, the control unit may allow movement of the actuation unit only if the tracking data show that the end effector is distant enough from the patient so as to avoid hitting him/her during said movement.

It is possible to make the actuation unit and planar mechanism sterile components, to be sterilized before each intervention. But, in a preferred embodiment, the actuation unit with its cables and equipped with the planar mechanism are covered by a single-use sterile drape. Additional components of the system can be also protected under the sterile drape. This has the advantage of facilitating and reducing cost of manufacturing and design, but also of being used easily for multiple consecutive surgeries without requiring re-sterilization of the device. The end effector itself is sterile, like any conventional surgical tool. Typically, it is sterilized before each intervention using autoclave. Different types of mechanical adaptors between the sterile drape and the end effector can be provided. Such adaptor does not require a very precise reproducible fixation if the saw contains a tracking element (described in more detail below), which increases the accuracy of the global system. The sterile drape covers the planar mechanism to facilitate the design and manufacturing of the device. For example, this design allows the use of ball-bearings mechanisms that would be difficult to autoclave.

Before cutting the anatomical structure, the user plans the intervention on the planning system, based on pre-operative and/or intra-operative medical images and data.

This planning step allows determining each target plane suited to perform the cut of the anatomical structure. It is specific to each application.

For example, as already described above, in the case of TKA, planning the implantation of a prosthesis on a knee usually results in the definition of five target planes on the femur and one on the tibia. It is also possible to define more than five cutting planes for fixing a prosthesis to a bone in order to optimize the shape of the prosthesis based on individual anatomy for example.

The planning system may form part of the surgical system according to the invention; otherwise, the planning system may be provided separately and connected to the control unit.

During the surgical intervention, the user may either use preoperative data/images together with intra-operative registration methods, or use directly intraoperative data/images. In both cases, the result of the planning consists of at least one target plane, the pose of each plane being determined in the coordinate system of the anatomical structure to be cut.

The pose of each target plane is then transferred to the control unit.

The control unit initializes its sub-systems and the device is ready to use.

Before starting the device, the articulated holding arm (if any) is moved by a user so as to bring the actuation unit in a rough suitable position relative to the anatomical structure, and is then locked. Then, the end effector is attached to the planar mechanism.

Once operation of the device has been started by the user, the tracking unit continuously feeds back tracking information to the control unit for recalculation and visualization purposes.

The system also comprises a tracking unit 200 configured to determine in real time the pose of the end effector with respect to the anatomical structure to be cut.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination. According to a preferred embodiment, the tracking system is based on passive optical technology.

The tracking unit comprises at least one tracker that may be attached to any component of the actuation unit, e.g. to one of the mobile segments.

The position of each component of the actuation unit is known in real time thanks to encoders or sensors of the motors, and a calibrated model of the robot that includes all axes and distances of the robot segments. Using this model, and well-known geometric modeling techniques in robotics, it is possible to calculate the relative positions of all segments, so if one measurement is known in a coordinate system attached to the robot basis using an external tracker, then any segment position is also known in the same coordinate system. Additionally, if a tracker is attached to the base of the actuation unit and a second tracker is attached to the anatomical structure, then the pose of any component of the actuation unit is known in the coordinate system attached to the tracker of the anatomical structure.

In addition, at least one tracker is rigidly attached to the patient's anatomical structure to be cut so as to allow localizing the cutting plane relative to the coordinate system of this anatomical structure to be cut.

Micro or macro motions of the robotic device with respect to the anatomical structure to be cut, including slow and fast motions, are compensated within a tolerance range and a given time frame that defines the precision of the device.

Typically, for bone surgery applications, motions in the range of a few tenths of a millimeter need to be compensated to obtain sufficient precision; such compensation requires ultrafast motion detection and measurement, as well as calculation of the compensation motion to be applied and execution of the desired compensation motion.

The compensation procedure cannot rely solely on the geometrical model of the robotic device, which is never perfect due to mechanical backlashes and irregularities, as well as structural deformations that are changing depending on the relative positions of the end effector and the various parts of the robotic device.

Another issue to be taken into account in the compensation procedure is that the planar mechanism itself may slightly bend, especially if it is made of a lightweight and compact structure. As a result, its components do not have the same position and orientation. Indeed, a variable shift on the position and orientation of the planar mechanism is observed, and the compensation of the end effector position is never perfect, preventing the robotic device from converging to the target plane. In such case, either the robotic device oscillates, or it converges to a position which is shifted from the target plane.

To improve the motion compensation, an additional tracker is rigidly attached to the end effector. This additional tracker allows determining reliably the position and orientation of the end effector in the coordinate system of the robotic device, taking into account any mechanical backlash that may exist between the actuation unit and the end effector.

Instead of attaching said additional tracker to the end effector, it is possible to rigidly attach it to the end of the planar mechanism opposite the actuation unit. Said end of the planar mechanism may comprise an interface capable of receiving any type of end effector as mentioned above (sagittal saw, reciprocal saw, burr . . . ) but also other surgical tools such as a drill guide to be used to drill the pegs for implanting the prosthesis, and/or a cutting guide, etc. For example, the drill guide can have a toothed end intended to grip into the surface of the anatomical structure where a hole has to be drilled. Advantageously, a handle is provided at the opposite end of the drill guide to facilitate its manipulation by the surgeon. Thus, once the toothed end has been applied to the anatomical structure, the surgeon can simply change the orientation of the drill guide thanks to a navigation interface. The drill may carry a tracker, instead of having the tracker carried by the end of the planar mechanism.

In case the planar mechanism comprises encoders, the position of each segment of the planar mechanism can be determined, which provides redundant information on the position of the end effector.

The compensation of relative motion between the robotic device and the anatomical structure using the additional tracker rigidly attached to the end effector or to the end of the planar mechanism may be implemented as follows, with reference to the control loop shown in FIG. 14.

The additional tracker allows relying on the actual position of the end effector or of the end of the planar mechanism instead of the theoretical position of the planar mechanism.

This greatly increases the confidence in the compensation mechanism.

Moreover, the association of the tracker attached to the end effector and the tracker attached to the actuation unit enables dynamic estimation of the alignment error between the two. This alignment error is then used to correct the position and orientation of the planar mechanism to the target plane.

Figure 14:
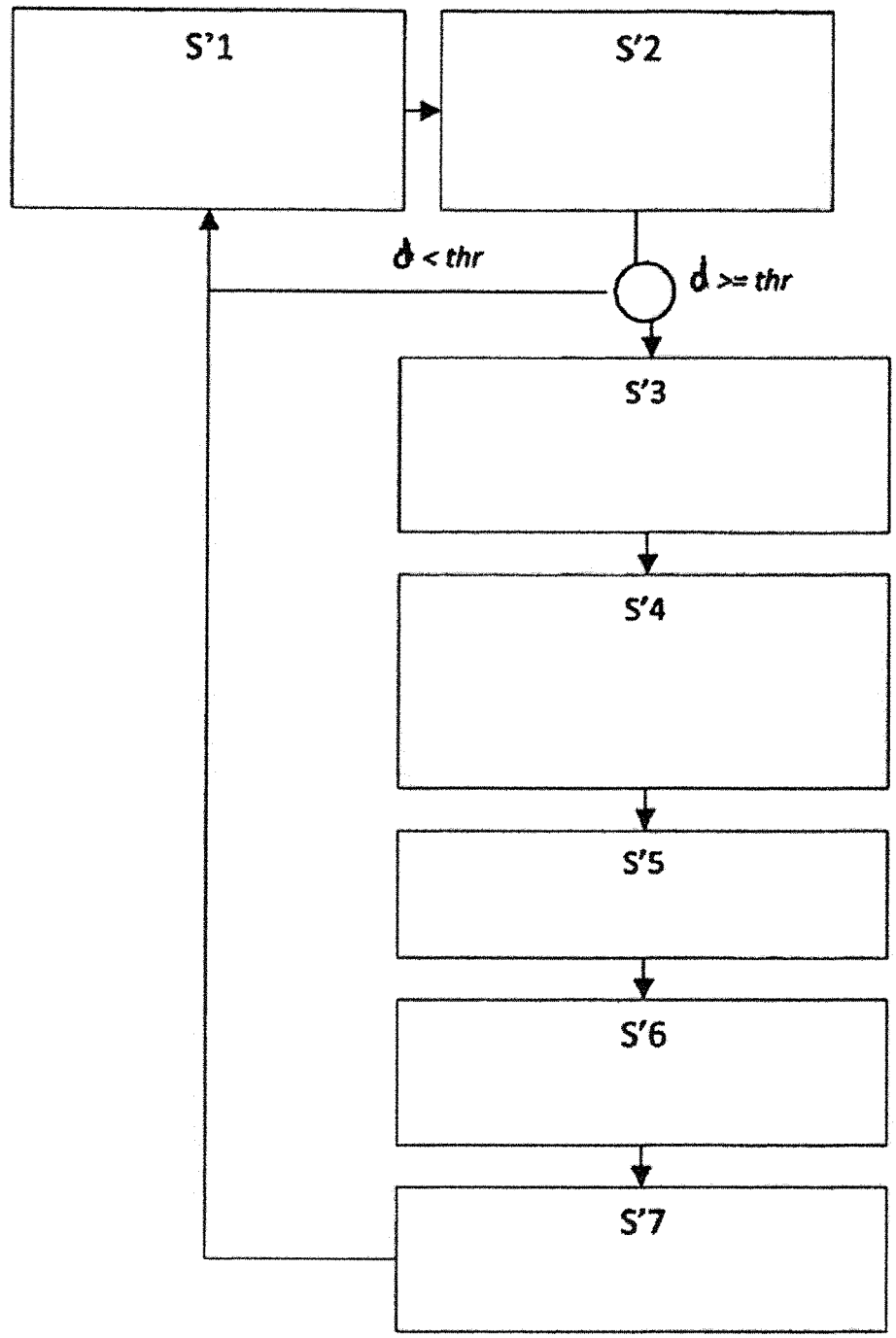
FIG. 14 represents a compensation control loop implemented by the control unit.

FIG. 14 is a flowchart describing the control loop allowing the compensation.

In step S'1, new poses of the robotic device, the end effector and the anatomical structure are determined using localization information provided by the trackers.

In step S'2, a deviation d between the plane of the end effector (cutting plane) and the target plane is computed.

If the deviation d is less than a threshold thr, the end effector can be operated and a new pose of the robotic device and anatomical structure is determined (step S'1).

If the deviation d is greater than or equal to the threshold thr, then in step S'3 the plane of the end effector (cutting plane) and the target plane are projected in the coordinate system of the robotic device.

In step S'4, a correction matrix $T_{err}$ corresponding to a rigid transformation between the plane of the planar mechanism and the plane of the end effector is computed.

In step S'5, the target plane is updated with $T_{err}$.

In step S'6, a new attitude of the robotic device is computed to reach the target plane. This computation determines the movements to be applied by the motors of the actuation unit.

In step S'7, the motors of the actuation unit are activated in accordance with step S'6.

Then, the new position of the robotic device and anatomical structure is determined (step S'1).

From this base algorithm, further improvements have proven to enhance the behavior of the robotic device:
- spatially filtering the positions of the various elements (for instance thanks to a Kalman filter or equivalent);
- averaging the estimation of $T_{err}$ in a given time frame, for instance thanks to quaternion averaging techniques. This allows reducing the potential oscillations due to small inconsistencies between the transformation estimation and the more complex reality of the mechanical links.

The correction matrix $T_{err}$ may vary depending on the current extension of the planar mechanism and therefore it is not constant. It also depends on the mechanical backlash and flexion of the planar mechanism, the position of the robot, and other factors. The correction matrix is calculated in real time, such that the deviation of $T_{err}$ between two calculations is not significant, considering reasonable motions of the saw by the user. This method of correction is extremely precise and efficient for compensating any mechanical defects, backlash and errors in the model.

It is to be noted that this compensation loop also allows at least partially compensating for backlash and flexion of the actuation unit.

Advantageously, the attachment of the trackers to the end effector and/or actuation unit is reversible and reproducible.

Throughout the set of drawings, a tracker attached to the anatomical structure is designated by reference 201, a tracker attached to the actuation unit or to the holding arm is designated by reference 202, and a tracker attached to the end effector is designated by reference 203.

As mentioned previously, a user interface is defined so as to indicate the user at least one potential position and orientation of the actuation unit suitable for aligning the cutting plane with a target plane.

From time to time, the user interface may provide information to the user to guide him or her to reposition the actuation unit in an optimal pose to enable alignment of the cutting plane with a target plane. The user interface may also indicate to the user if all targeted cutting planes can be reached from the current position of the actuation unit, and if not, in which direction to move to reach an optimal position.

Said user interface may be visual and/or acoustic.

According to an embodiment, the user interface may comprise a screen connected to the control unit, e.g. the screen 400 shown on FIG. 2.

If a realistic 3D model of the anatomical structure is available (i.e. obtained by pre-operative or per-operative imaging of the patient), it may be displayed on the screen, along with a real-time representation of the end effector (e.g. envelope of the oscillating blade). Such a visualization is made possible by obtaining tracking data from the tracker attached to the end effector or, if any, by obtaining position information from the encoders of the planar mechanism. For instance, if the end effector is a saw, the user can visualize the position of the tip of the saw blade relative to the bone, to ensure that the tip of the saw blade does not exit from the bone.

During the use of the device the control system checks in real time if the saw can be aligned with a target plane. If the robotic device is moved such that the saw cannot be aligned with said target plane—e.g. in case of vibrations, and/or an involuntary movement of the patient, then the information provided to the user may change, e.g. the color of the arrow is changed or an acoustical feedback is produced.

According to another embodiment (not shown), the user interface comprises visual indicators such as LEDs. These LEDs may be arranged on a supporting surface that is fixed to the robotic device. Alternatively, the LEDs may be arranged on a support separate from the robotic device and connected to it by a wire. Alternatively, the LEDs may be arranged on a support separate from the robotic device and wirelessly linked to the robotic device. Such a separate support can be placed in the vicinity of the robotic device/end effector, in the user's field of view.

Said indicators are intended to instruct the user not to activate the end effector, in case the robotic device is not able to compensate for a misalignment between the cutting plane and the target plane. For example, a red and blinking light is turned on as soon as the trackers mounted on the anatomical structure and/or the end effector are not visible. It is turned off or changed to a green light as soon as the visibility of trackers is restored.

Another way of providing information to the user is to use numerical displays (e.g. provided by LCD screens) that represent virtual spirit levels. The general orientation of the robotic device can be adjusted by the user based on one virtual spirit level on top of the robotic device and another one on a side (opposite to the patient's leg) of the robotic device. The distance of the robotic device can be adjusted using a support unit, and/or using indicators such as LEDs representing an arrow pointing the desired direction, and/or via the screen of the user interface.

The system further comprises a control unit which is intended to control the pose of the saw in an optimal way in order to align it with a target plane.

According to an embodiment, the control unit may be coupled to the end effector used to perform the cut and configured to allow the actuation of the end effector only when the cutting plane is aligned with the target plane. This increases the safety of the system.

Figure 15:
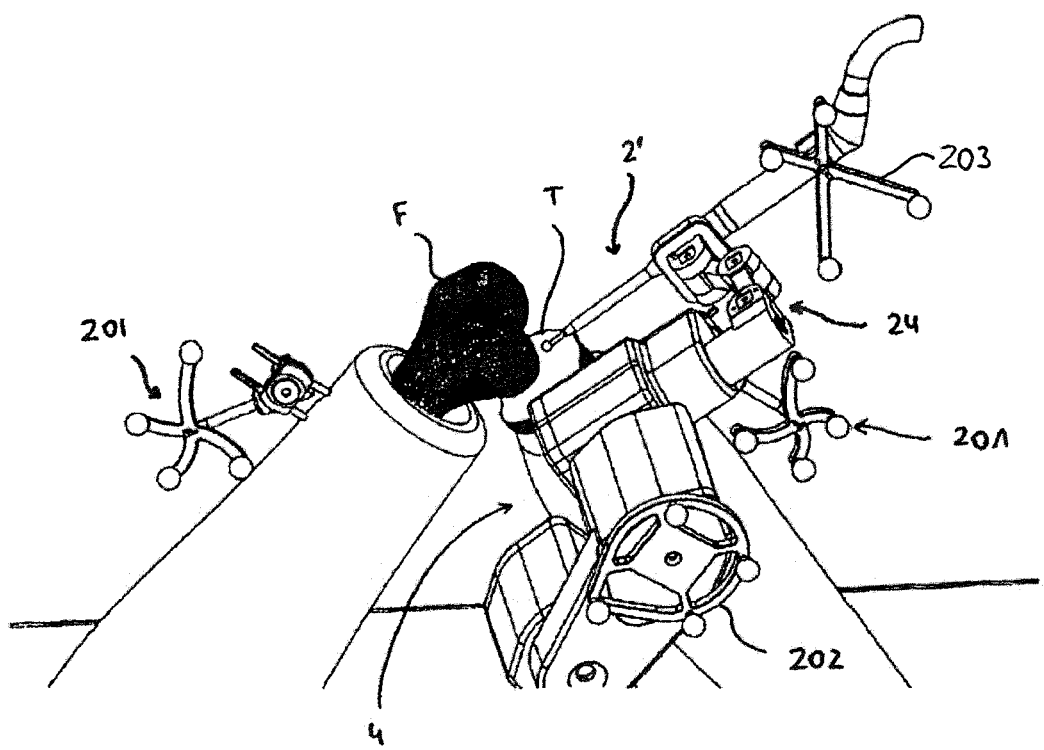
FIG. 15 illustrates an embodiment of the robotic device wherein the end effector is a burr.

FIG. 15 illustrates a setup of the robotic device, with a burr 2' as the end effector.

Although the trackers illustrated in the figures are optical trackers, it should be noted that any other tracking technology (e.g. electromagnetic) may be used. For example, the terminal part of the actuation unit could be provided with an electromagnetic emitter and the end effector with an electromagnetic receiver.

It should be noted that the embodiments described above may be combined.

REFERENCES

[Roth et al] M. Roth, Ch. Brack, A. Schweikard, H. Götte, J. Moctezuma, F. Goss, "A new less invasive approach to knee surgery using a vision-guided manipulator", December 2000

The invention claimed is:

1. A computer-assisted surgical system, comprising:
an end effector having an attached tracker;
an actuation unit for adjusting a position and orientation of the end effector, wherein the actuation unit has at least three motorized degrees of freedom;
a passive planar mechanism connecting the actuation unit to the end effector; and
a control unit configured to:
determine a pose of the end effector using data from sensing of the tracker;
determine a cutting plane based on the pose of the end effector;
compare the cutting plane to a target plane for an anatomical structure of a patient; and
control the actuation unit to bring the cutting plane into alignment with the target plane.

2. The computer-assisted surgical system of claim 1, wherein the cutting plane is parallel to a plane of the planar mechanism.

3. The computer-assisted surgical system of claim 1, wherein the cutting plane is orthogonal to a plane of the planar mechanism.

4. The computer-assisted surgical system of claim 1, wherein the end effector comprises a surgical saw comprising a saw blade configured to oscillate within the cutting plane.

5. The computer-assisted surgical system of claim 1, wherein the end effector comprises a burr, a laser, a high-pressure water jet, a scalpel, or a lancet.

6. The computer-assisted surgical system of claim 1, further comprising a passive lockable articulated arm holding the actuation unit.

7. The computer-assisted surgical system of claim 1, wherein the planar mechanism comprises at least two segments connected by a joint which defines an articulation axis between the segments.

8. The computer-assisted surgical system of claim 7, further comprising an encoder, wherein the joint is associated with the encoder for determining a position of each segment.

9. The computer-assisted surgical system of claim 7, further comprising a locking system to lock the joint in position.

10. The computer-assisted surgical system of claim 7, further comprising stops configured to limit a range of rotation of the segments around the joint.

11. The computer-assisted surgical system of claim 10, wherein the stops are bulges extending radially outwardly from the joint.

12. The computer-assisted surgical system of claim 7, further comprising a locking system for locking the end effector to the actuation unit in a rest position.

13. The computer-assisted surgical system of claim 1, further comprising a locking system for locking the end effector to the actuation unit in a rest position.

14. The computer-assisted surgical system of claim 13, wherein the locking system comprises a support coupled between the actuation unit and an intermediate part attached to the end effector.

15. The computer-assisted surgical system of claim 14, wherein the support comprises:
an opening for receiving a protrusion from the intermediate part.

16. The computer-assisted surgical system of claim 14, wherein the support comprises a magnet or an electromagnet for reversibly engaging a magnetic element of the intermediate part.

17. A method of using the computer-assisted surgical system of claim 1, comprising:
determining poses of the actuation unit, the end effector, and the anatomical structure using localization information provided by a tracking unit;
computing a deviation between the cutting plane and the target plane; and
if the deviation is less than a threshold, allowing operation of the end effector; and
if the deviation is greater than or equal to the threshold, not allowing operation of the end effector.

18. The method of claim 17, further comprising, if the deviation is greater than or equal to the threshold:
projecting the cutting plane and the target plane in a coordinate system of the actuation unit;
computing a transformation between a plane of the planar mechanism and the cutting plane;
updating the target plane with the transformation;
computing a new attitude of the actuation unit to align the cutting plane with the updated target plane; and
moving the actuation unit to bring the cutting plane into alignment with the updated target plane.

19. The method of claim 18, further comprising:
after moving the actuation unit, determining poses of the actuation unit, the end effector, and the anatomical structure;
computing a deviation between the cutting plane and the updated target plane; and
if the deviation is less than a threshold, allowing operation of the end effector.

20. A computer-assisted surgical system, comprising:
an end effector having an attached tracker;
an actuation unit for adjusting a position and orientation of the end effector, wherein the actuation unit has at least three motorized degrees of freedom;
a passive planar mechanism connecting the actuation unit to the end effector;
a locking system for locking the end effector to the actuation unit in a rest position; and
a control unit configured to:
determine a pose of the end effector using data from sensing of the tracker;
determine a cutting plane based on the pose of the end effector;
compare the cutting plane to a target plane for an anatomical structure of a patient; and
control the actuation unit to bring the cutting plane into alignment with the target plane, wherein the control unit is configured to allow movement of the actuation unit only if the rest position is detected.

* * * * *